United States Patent
Zhou et al.

(10) Patent No.: US 10,888,848 B2
(45) Date of Patent: Jan. 12, 2021

(54) CATALYTIC CRACKING CATALYST AND PREPARATION THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Lingping Zhou, Beijing (CN); Weilin Zhang, Beijing (CN); Mingde Xu, Beijing (CN); Zhenyu Chen, Beijing (CN); Huiping Tian, Beijing (CN); Yuxia Zhu, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 0 days.

(21) Appl. No.: 16/484,418

(22) PCT Filed: Feb. 12, 2018

(86) PCT No.: PCT/CN2018/076430
§ 371 (c)(1),
(2) Date: Aug. 7, 2019

(87) PCT Pub. No.: WO2018/153302
PCT Pub. Date: Aug. 30, 2018

(65) Prior Publication Data
US 2019/0351396 A1 Nov. 21, 2019

(30) Foreign Application Priority Data

Feb. 22, 2017 (CN) .......................... 2017 1 0096449
Feb. 22, 2017 (CN) .......................... 2017 1 0097154

(51) Int. Cl.
| | | |
|---|---|---|
| *B01J 29/06* | (2006.01) | |
| *B01J 29/08* | (2006.01) | |
| *B01J 35/10* | (2006.01) | |
| *C01B 39/24* | (2006.01) | |
| *C10G 11/04* | (2006.01) | |
| *B01J 35/00* | (2006.01) | |

(Continued)

(52) U.S. Cl.
CPC .......... *B01J 29/084* (2013.01); *B01J 29/085* (2013.01); *B01J 29/088* (2013.01); *B01J 35/002* (2013.01); *B01J 35/0006* (2013.01); *B01J 35/109* (2013.01); *B01J 35/1038* (2013.01); *B01J 35/1042* (2013.01); *B01J 35/1061* (2013.01); *B01J 35/1066* (2013.01); *B01J 37/0009* (2013.01); *B01J 37/0045* (2013.01); *B01J 37/0201* (2013.01); *B01J 37/10* (2013.01); *B01J 37/28* (2013.01); *B01J 37/30* (2013.01); *C01B 39/24* (2013.01); *C10G 11/04* (2013.01); *B01J 2229/32* (2013.01); *B01J 2229/36* (2013.01); *B01J 2229/42* (2013.01); *C07C 2529/06* (2013.01); *C07C 2529/08* (2013.01); *C10G 2300/70* (2013.01)

(58) Field of Classification Search
CPC ...... B01J 29/084; B01J 29/085; B01J 29/088; B01J 2229/32; B01J 2229/42; B01J 2229/36; B01J 35/1066; B01J 35/002; B01J 35/0006; B01J 35/1061; B01J 35/1038; B01J 35/1042; B01J 35/109; B01J 37/0009; B01J 37/0201; B01J 37/28; B01J 37/0045; B01J 37/10; B01J 37/30; C07C 2529/06; C07C 2529/08; C10G 2300/70
USPC .......... 502/60, 61, 63, 64, 65, 68, 69, 73, 79
See application file for complete search history.

(56) References Cited

U.S. PATENT DOCUMENTS 4,480,047 A * 10/1984 Beck ...................... B01J 29/084
502/65
5,069,890 A 12/1991 Dai et al.
(Continued)

FOREIGN PATENT DOCUMENTS

| CN | 1031030 A | 2/1989 |
|---|---|---|
| CN | 1098130 A | 2/1995 |

(Continued)

OTHER PUBLICATIONS

Jianhui Zhao et al., "Study on Chemical Modification of Ultra-stable Y Molecular Sieve", QILU Petrochemical Technology, 2000, vol. 28, No. 1, pp. 36-39.

(Continued)

*Primary Examiner* — Elizabeth D Wood
(74) *Attorney, Agent, or Firm* — Novick, Kim & Lee, PLLC; Allen Xue

(57) ABSTRACT

A catalytic cracking catalyst has a rare earth modified Y-type molecular sieve, an additive-containing alumina binder, and a clay. The rare earth modified Y-type molecular sieve has a rare earth oxide content of about 4-12 wt %, a phosphorus content of about 0-10 wt %, a sodium oxide content of no more than about 1.0 wt %, a total pore volume of about 0.36-0.48 mL/g, a percentage of the pore volume of secondary pores having a pore size of 2-100 nm to the total pore volume of about 20-40%, a lattice constant of about 2.440-2.455 nm, a percentage of non-framework aluminum content to the total aluminum content of no more than about 10%, a lattice collapse temperature of not lower than about 1060° C., and a ratio of B acid to L acid in the total acid content of the modified Y-type molecular sieve of no less than about 3.50.

20 Claims, 1 Drawing Sheet

(51) Int. Cl.
*B01J 37/28* (2006.01)
*B01J 37/02* (2006.01)
*B01J 37/00* (2006.01)
*B01J 37/10* (2006.01)
*B01J 37/30* (2006.01)

(56) References Cited

U.S. PATENT DOCUMENTS

| | | | |
|---|---|---|---|
| 5,087,348 A | | 2/1992 | Dai et al. |
| 5,559,067 A | * | 9/1996 | Lerner .................. B01J 29/084 |
| | | | 502/68 |
| 5,601,798 A | | 2/1997 | Cooper et al. |
| 2003/0136707 A1 | * | 7/2003 | Harris .................. B01J 35/0026 |
| | | | 208/120.01 |
| 2013/0131419 A1 | | 5/2013 | Buchanan et al. |
| 2014/0299511 A1 | | 10/2014 | Luo et al. |
| 2015/0151284 A1 | | 6/2015 | Gao et al. |

FOREIGN PATENT DOCUMENTS

| | | |
|---|---|---|
| CN | 1127161 A | 7/1996 |
| CN | 1194941 A | 10/1998 |
| CN | 1317547 A | 10/2001 |
| CN | 1330981 A | 1/2002 |
| CN | 1353086 A | 6/2002 |
| CN | 1362472 A | 8/2002 |
| CN | 1388064 A | 1/2003 |
| CN | 1436727 A | 8/2003 |
| CN | 1132898 C | 12/2003 |
| CN | 1506161 A | 6/2004 |
| CN | 1629258 A | 6/2005 |
| CN | 1727442 A | 2/2006 |
| CN | 1727445 A | 2/2006 |
| CN | 1915485 A | 2/2007 |
| CN | 1915486 A | 2/2007 |
| CN | 1916116 A | 2/2007 |
| CN | 101285001 A | 10/2008 |
| CN | 101745418 A | 6/2010 |
| CN | 101767029 A | 7/2010 |
| CN | 102020289 A | 4/2011 |
| CN | 103159227 A | 6/2013 |
| CN | 103449471 A | 12/2013 |
| CN | 103787352 A | 5/2014 |
| CN | 104229823 A | 12/2014 |
| RU | 2509605 C1 | 3/2014 |

OTHER PUBLICATIONS

"Petrochemical Analysis Methods (RIPP Test Methods)", edited by Cuiding Yang et al., Science Press, Sep. 1990, First Edition, pp. 263-268, 412-415 and 424-426, ISBN: 7-03-001894-X.

* cited by examiner

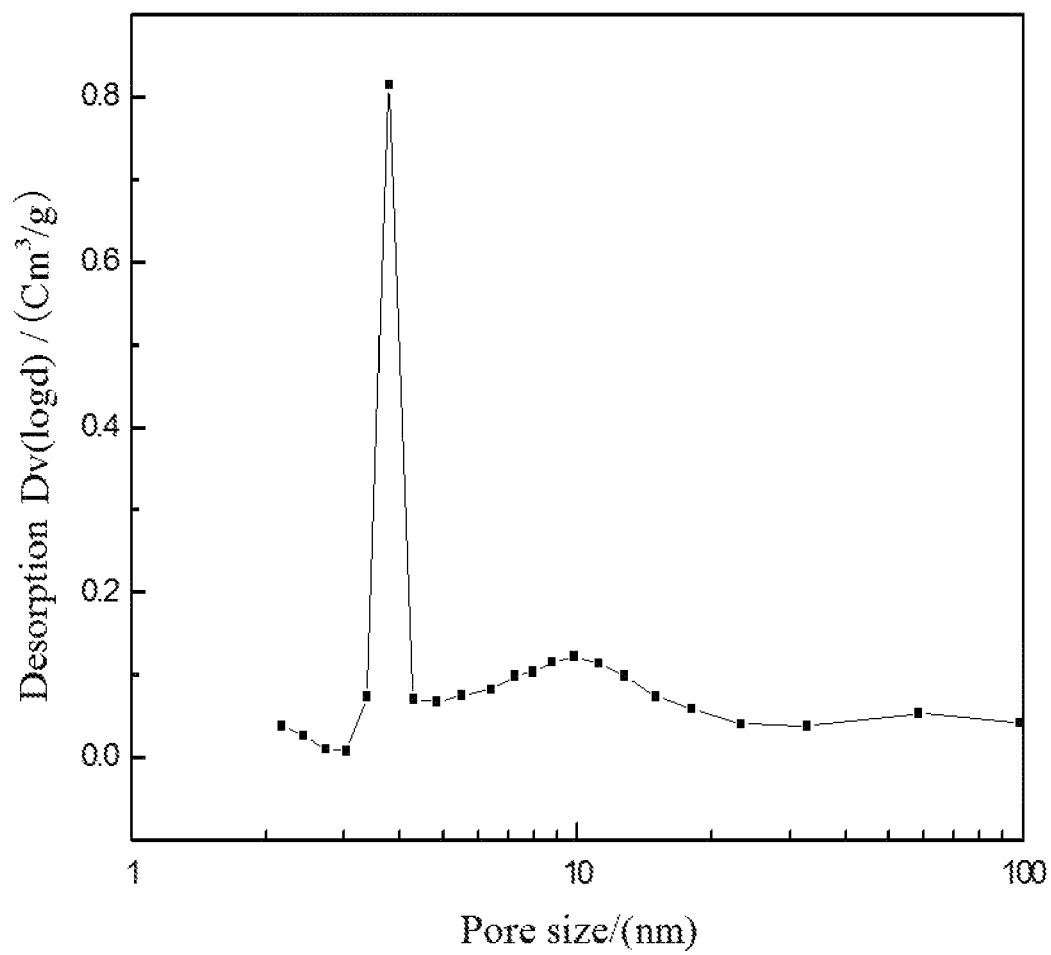
Dual probable pore size distribution of the molecular sieve according to the present application

US 10,888,848 B2

CATALYTIC CRACKING CATALYST AND PREPARATION THEREOF

TECHNICAL FIELD

The present application relates to a catalytic cracking catalyst based on a modified Y-type molecular sieve and preparation thereof.

BACKGROUND ART

Since its first use in the 1960s, Y-type molecular sieves have been the main active component of fluid catalytic cracking (FCC) catalysts. However, as crude oils become heavier, the content of polycyclic compounds in FCC feedstocks increases significantly, while their ability to diffuse in the pores of molecular sieves decreases significantly. When catalysts comprising Y-type molecular sieves as the main active component are directly used to process heavy fractions such as residual oils, the accessibility of the active center of the catalysts will become a major obstacle to the cracking of polycyclic compounds contained therein, since Y-type molecular sieves used as the main active component have a pore size of only 0.74 nm.

The pore structure of molecular sieves is closely related to the cracking performance, especially for residue cracking catalysts. Secondary pores of molecular sieves can increase the accessibility of macromolecules of residual oils to the active center of catalysts, thereby improving their cracking capability for residual oils. Hydrothermal dealuminization method is one of the most widely used methods for preparing ultra-stable molecular sieves in the industry. The method comprises firstly subjecting a NaY molecular sieve to ion-exchange with an aqueous solution containing ammonium ions to reduce the content of sodium ion in the molecular sieve, and then subjecting the ammonium ion-exchanged molecular sieve to roasting at 600-825° C. in steam atmosphere to allow it to be ultra-stabilized. The method is cost-effective and is easy to be industrialized for large-scale production, and the ultra-stable Y-type molecular sieve thus obtained is rich in secondary pores, but there is a serious loss in the crystallinity of the molecular sieve and the thermal stability thereof is poor.

At present, the production for ultra-stable Y-type molecular sieves used in the industry is normally based on an improvement on the above-mentioned hydrothermal roasting method. A method comprising two ion-exchange stages and two roasting stages can be adopted, and the ultra-stable Y molecular sieve obtained thereby may also have a certain amount of secondary pores. However, the proportion of secondary pores having a relatively large pore size in the total secondary pores is low, and the specific surface area and crystallinity of the ultra-stable molecular sieves need to be further improved.

U.S. Pat. Nos. 5,069,890 and 5,087,348 disclose a method for the preparation of mesoporous Y-type molecular sieves, comprising the step of subjecting a commercially available USY raw material to a treatment at 760° C. in 100% steam atmosphere for 24 hours. The mesopore volume of the Y-type molecular sieve obtained by this method is increased from 0.02 mL/g to 0.14 mL/g, but its crystallinity is decreased from 100% to 70%, its specific surface area is decreased from 683 m²/g to 456 m²/g, and its acid density is dropped dramatically from 28.9% to 6%.

U.S. Pat. No. 5,601,798 discloses a method for the preparation of mesoporous Y-type molecular sieves, comprising the steps of mixing HY or USY raw material in an autoclave with a $NH_4NO_3$ solution or a mixed solution of $NH_4NO_3$ and $HNO_3$, and subjecting the mixture to a treatment at a temperature of 115-250° C. above its boiling point for 2-20 hours. The mesoporous molecular sieve thus obtained may have a mesopore volume of up to 0.2-0.6 mL/g, but its crystallinity and specific surface area are significantly decreased.

CN104229823A discloses a method for the combined modification of mesoporous ultra-stable Y molecular sieves, which is characterized in that an organic acid dealuminating agent and an inorganic salt dealuminating agent are simultaneously added during the modification to conduct a combined organic acid-inorganic salt modification. The optimum operation conditions such as optimum concentrations of the organic acid and inorganic salt solutions, volume ratio, reaction time and reaction temperature can be determined by orthogonal test. The USY molecular sieve obtained by this method shows a significantly increased secondary pore content than the industrial USY molecular sieve, and is suitable for as a support in hydrocracking catalysts for producing more middle distillate. CN1388064A discloses a method for the preparation of high-silica Y-type zeolites having a lattice constant of 2.420-2.440 nm, comprising the steps of subjecting a NaY zeolite or an ultra-stabilized Y-type zeolite to one or more stages of ammonium exchange, hydrothermal treatment and/or chemical dealumination, characterized in that at least the first ammonium exchange stage prior to the hydrothermal treatment and/or chemical dealumination of the ammonium exchange stage(s) is a low-temperature selective ammonium exchange conduceted at a temperature of from room temperature to below 60° C., and other ammonium exchange stage(s) is either a low-temperature selective ammonium exchange conducted at a temperature of from room temperature to below 60° C. or a conventional ammonium exchange conducted at 60-90° C. The high-silica Y-type zeolite obtained in this patent application shows a high retention of crystallinity at a small lattice constant and has more secondary pores, and is suitable for middle distillate hydrocracking catalysts. The ultra-stable Y molecular sieves prepared by the methods disclosed in the above documents comprise a certain amount of secondary pores, have a small lattice constant and a relatively high silica-alumina ratio, and contain no rare earth. They are suitable for hydrogenation catalysts, but are difficult to statisfy the high catalystic cracking activity required for the processing of heavy oils.

CN1629258A discloses a method for the preparation of a cracking catalyst containing a rare earth modified ultra-stable Y-type molecular sieve, comprising the steps of contacting a NaY molecular sieve with an aqueous ammonium salt solution containing 6-94% by weight of the ammonium salt under atmospheric pressure at a temperature of from greater than 90° C. to no more than the boiling point of the aqueous ammonium salt solution at a weight ratio of the ammonium salt to the molecular sieve ranging from 0.1-24 for two or more times to reduce the $Na_2O$ content of the molecular sieve to less than 1.5% by weight; contacting the treated molecular sieve with an aqueous solution having a rare earth salt concentration of 2-10% by weight at 70-95° C. to obtain a modified molecular sieve comprising 0.5-18% by weight of the rare earth, calculated based on $RE_2O_3$, and then mixing the modified molecular sieve with a support and drying. The molecular sieve thus obtained is not sufficiently ultra-stablized, and has a relatively low silica-alumina ratio, and less secondary pores.

CN1127161A discloses a method for the preparation of a rare earth modified silica-rich ultra-stable Y-type molecular sieve, in which NaY is used as a feedstock, and a gas phase Si—Al isomorphous substitution reaction is carred out with $SiCl_4$ in the presence of solid $RECl_3$ to complete the ultra-stabilization and the rare earth ion-exchange of the NaY in a single step. The molecular sieve obtained by the method has a lattice constant $a_0$ of 2.430-2.460 nm, a rare earth content of 0.15-10.0% by weight, and a $Na_2O$ content of less than 1.0% by weight. However, the molecular sieve is prepared by using only the gas phase ultra-stabilization method, and thus, though an ultra-stable Y molecular sieve containing rare earth can be obtained, the molecular sieve obtained lacks secondary pores.

In gas phase chemical methods, an isomorphous substitution reaction occurs under gas phase ultra-stablization conditions, where the aluminum in the framework of the molecular sieve is directly substituted by the silicon in the gaseous silicon tetrachloride, so that the aluminium removal and silicon supplementation are carried out simultaneously, and a uniform dealumination can be achieved. However, gas phase ultra-stablized molecular sieves have no secondary pores.

CN1031030A discloses a method for the preparation of ultra-stable Y-type molecular sieves with low rare earth content, in which an ultra-stable Y-type molecular sieve with low rare earth content for the cracking of hydrocarbons is prepared by the step of subjecting a NaY-type molecular sieve raw material to a single stage of combined ion-exchange with ammonium and rare earth ions, and then to stabilization treatment, partial removal of framework aluminum atoms, thermal or hydrothermal treatment, and the like. The molecular sieve has a rare earth content ($RE_2O_3$) of 0.5-6 wt %, a $SiO_2/Al_2O_3$ ratio of 9-50, and a lattice constant $a_0$ of 2.425-2.440 nm. The ultra-stable molecular sieve obtained by the method has a high silica-alumina ratio and a small lattice constant, and contains a certain amount of rare earth. However, the molecular sieve obtained shows a poor catalytic cracking activity for heavy oils and a poor coke selectivity.

CN1330981A discloses a phosphorus-modified Y-type zeolite and preparation thereof, in which the phosphorus-modified Y-type zeolite comprises phosphorus, a silicon component and a rare earth component, and the silicon component is supported by impregnating the zeolite with a solution of a silicon compound, the silicon component is present in an amount of 1 to 15% by weight calculated on the basis of $SiO_2$, the phosphorus component is present in amount of 0.1 to 15% by weight calculated on the basis of $P_2O_5$, and the rare earth component is present in an amount of 0.2 to 15% by weight calculated on the basis of rare earth oxides. The molecular sieve is prepared by impregnating a rare earth-containing Y-type zeolite with a solution containing silicon and phosphorus, drying, and then subjecting the resultant to hydrothermal roasting at 550-850° C. However, the phosphorus-modified Y-type zeolite shows a low cracking activity for heavy oils, and a low yield of light oil.

CN1353086A discloses a method for the preparation of Y-type molecular sieves containing phosphorus and rare earth, compriseing the steps of subjecting a NaY molecular sieve to combined ion-exchange with ammonium and rare earth ions and hydrothermal roasting, then reacting with a phosphorus compound to incorporate thereinto 0.2-10% by weight of phosphorus (calculated on the basis of $P_2O_5$), and subjecting the resultant to hydrothermal roasting again. However, the phosphorus-containing Y-type zeolite shows a low cracking activity for heavy oils, and a low yield of light oil.

CN1506161A discloses a rare earth modified ultra-stable Y molecular sieve active component, which comprises 8-25% by weight of rare earth oxides, 0.1-3.0% by weight of phosphorus, and 0.3-2.5% by weight of sodium oxide, and has a crystallinity of 30-55% and a lattice constant of 2.455-2.472 nm. To obtain the molecular sieve, a NaY zeolite raw material is subjected to ion-exchange with rare earth and to a first roasting to produce an "one-time ion exchange and one-time roasting" rare earth modified NaY zeolite, and then reacted with rare earth, a phosphorus-containing material and an ammonium salt, and subjected to a second roasting to produce a phosphorus and rare earth modified Y zeolite. The molecular sieve thus obtained has a high rare earth content, a large lattice constant, a poor thermal stability, and a poor coke selectivity.

CN1317547A discloses a phosphorus and rare earth modified Y-type zeolite and preparation thereof, the molecular sieve being obtained by subjecting a NaY zeolite to combined ion-exchange with rare earth and ammonium salt, hydrothermal roasting, reaction with a phosphorus compound, and then to a second roasting, in which the weight ratio of $RE_2O_3$/Y zeolite is 0.02-0.18, the weight ratio of ammonium salt/Y zeolite is 0.1-1.0, the weight ratio of P/Y zeolite is 0.003-0.05, the roasting temperature is 250-750° C., the atmosphere is 5-100% steam atmosphere, and the time is 0.2-3.5 hours. The modified Y-type zeolite thus obtained shows a poor thermal stability and a poor cracking activity for heavy oils.

CN1436727A provides a method for the preparation of "one-time ion exchange and one-time roasting" modified faujasite zeolites, comprising the steps of subjecting a faujasite zeolite to one stage of ion-exchange with a phosphorus compound and an ammonium compound, and subjecting the ion-exchanged slurry to a further reaction by introducing thereinto a rare earth solution, and then to filtering, washing, and roasting in steam atmosphere. The zeolite thus obtained shows a low cracking activity and a low heavy oil conversion.

In addition, the liquid phase Si—Al isomorphous substitution method using $(NH_4)_2SiF_6$ is also a common used method for the preparation of ultra-stable molecular sieves, of which the mechanism is to replace the Al atoms in the framework of the molecular sieve with Si in the $(NH_4)_2SiF_6$ in solution, so that an ultra-stable molecular sieve with an increased silica-alumina ratio can be produced. The Si—Al isomorphous substitution method using $(NH_4)_2SiF_6$ is characterized in that an ultra-stable zeolite with a framework $SiO_2/Al_2O_3$ molar ratio of 10-30 or higher can be produced, which has a high thermal stability, no non-framework aluminum or $Al_2O_3$ fragments, and a high relative crystallinity. However, due to the diffusion problem, the dealumination with $(NH_4)_2SiF_6$ is nonuniform and may cause a deficiency of surface Al, which is called "surface enrichment of silicon". In addition, the insoluble substance $AlF_3$ generated during the dealumination with $(NH_4)_2SiF_6$ and the residual fluorosilicate may affect the hydrothermal stability of the molecular sieve, $(NH_4)_2SiF_6$ may cause an environmental pollution, and the ultra-stable molecular sieve obtained lacks secondary pores.

SUMMARY OF THE INVENTION

It is an object of the present application to provide a catalytic cracking catalyst containing a modified Y-type molecular sieve that is suitable for catalytic cracking of heavy oils and preparation thereof, which shows a higher cracking activity for heavy oils and a better coke selectivity.

In an aspect, the present application provides a catalytic cracking catalyst, comprising, based on the weight of the catalytic cracking catalyst, from about 10% to about 50% by weight, on a dry basis, of a rare earth modified Y-type molecular sieve, about 2% to about 40% by weight, on a dry basis, of an additive-containing alumina and about 10% to about 80% by weight, on a dry basis, of clay; wherein the additive-containing alumina comprises, on a dry basis and based on the weight of the additive-containing alumina, about 60% to about 99.5% by weight of alumina and about 0.5% to about 40% by weight of an additive that is one or more selected from the group consisting of compounds containing alkaline earth metal, lanthanide metal, silicon, gallium, boron and/or phosphorus; the rare earth modified Y-type molecular sieve has a rare earth oxide content of about 4% to about 12% by weight, a phosphorus content of about 0% to about 10% by weight on the basis of $P_2O_5$, a sodium oxide content ($Na_2O$ content) of no more than about 1.0% by weight, a total pore volume of about 0.36 mL/g to about 0.48 mL/g, a percentage of the pore volume of secondary pores having a pore size of 2-100 nm to the total pore volume of the modified Y-type molecular sieve of about 20% to about 40%, a lattice constant of about 2.440-2.455 nm, a percentage of non-framework aluminum content to the total aluminum content of the modified Y-type molecular sieve of no more than about 10%, a lattice collapse temperature of not lower than about 1060° C., and a ratio of B acid to L acid in the total acid content of the modified Y-type molecular sieve of no less than about 3.5, as determined by pyridine adsorption infrared spectroscopy at 200° C.

In another aspect, the present application provides a method for the preparation of a catalytic cracking catalyst, comprising the steps of providing a rare earth modified Y-type molecular sieve, forming a slurry comprising the rare earth modified Y-type molecular sieve, an additive-containing alumina, clay, and water, and spray drying, wherein the additive-containing alumina comprises, based on the weight of the additive-containing alumina, 60% to 99.5% by weight of alumina and 0.5% to 40% by weight of an additive that is one or more selected from the group consisting of compounds containing alkaline earth metal, lanthanide metal, silicon, gallium, boron and/or phosphorus; the rare earth modified Y-type molecular sieve has a rare earth oxide content of about 4% to about 12% by weight, a phosphorus content of about 0% to about 10% by weight on the basis of $P_2O_5$, a sodium oxide content of no more than about 1.0% by weight, a total pore volume of about 0.36 mL/g to about 0.48 mL/g, a percentage of the pore volume of secondary pores having a pore size of 2-100 nm to the total pore volume of the modified Y-type molecular sieve of about 20% to about 40%, a lattice constant of about 2.440 nm to about 2.455 nm, a percentage of non-framework aluminum content to the total aluminum content of the modified Y-type molecular sieve of no more than about 10%, a lattice collapse temperature of not lower than about 1060° C., and a ratio of B acid to L acid in the total acid content of the modified Y-type molecular sieve of no less than about 3.5, as determined by pyridine adsorption infrared spectroscopy at 200° C.

In a preferred embodiment, the step of providing a rare earth modified Y-type molecular sieve comprises preparing the rare earth modified Y-type molecular sieve by the following steps:

(1) contacting a NaY molecular sieve with a rare earth salt solution for ion-exchange reaction, to obtain a rare earth modified Y-type molecular sieve having a reduced sodium oxide content;

(2) subjecting the Y-type molecular sieve obtained in the step (1) to roasting at a temperature of about 350° C. to about 520° C. in an atmosphere containing about 30 vol % to about 90 vol % of steam for about 4.5 hours to about 7 hours, to obtain a Y-type molecular sieve having a reduced lattice constant;

(3) contacting and reacting the Y-type molecular sieve obtained in the step (2) with gaseous silicon tetrachloride at a weight ratio of $SiCl_4$ to the Y-type molecular sieve on a dry basis ranging from about 0.1:1 to about 0.7:1 and a reaction temperature of about 200° C. to 650° C. for a reaction time of about 10 minutes to about 5 hours, to obtain a gas phase ultra-stabilized Y-type molecular sieve;

(4) contacting the modified Y-type molecular sieve obtained in the step (3) with an acid solution; and (5) optionally, subjecting the acid-treated modified Y-type molecular sieve obtained in the step (4) to phosphorus modification by contacting with a phosphorus compound.

The catalytic cracking catalyst provided in the present application has high thermal and hydrothermal stability and a high activity; and when used for catalytic cracking of heavy oils, the catalyst shows high cracking activity for heavy oils, excellent coke selectivity, and higher gasoline yield, light oil yield and total liquid yield.

The step of preparing the rare earth modified Y-type molecular sieve in the method for the preparation of the catalytic cracking catalyst provided in the present application can be used to produce high-silica Y-type molecular sieves rich in secondary pores with high crystallinity, high thermal stability and high hydrothermal stability, and can greatly improve the degree of ultra-stable treatment of the molecular sieve while maintaining a high crystallinity. The molecular sieve obtained has a uniform distribution of aluminum with low non-framework aluminum content, and unobstructed secondary pores. When used for catalytic cracking of heavy oils, the modified Y-type molecular sieve shows good coke selectivity, high cracking activity for heavy oils, and increased gasoline yield, light oil yield and total liquid yield.

The catalyst according to the present application is suitable for catalytic cracking of various hydrocarbon oils, and is especially suitable for catalytic cracking of heavy oils, and suitable hydrocarbon oils include, but not limited to, atmospheric residue, vacuum residue, vacuum gas oil, atmospheric gas oil, straight-run gas oil, light/heavy propane deasphalted oil and coker gas oil.

BRIEF DESCRIPTION OF THE DRAWINGS

The drawings, which form a part of the description, are provided to assist in further understanding of the present application and to further illustrate the present application in conjunction with the embodiments described hereinbelow, and are not intented to limit the present invention in any manner. In the drawings:

FIG. 1 is a schematic diagram showing a dual probable pore size distribution of the modified Y-type molecular sieve according to the present application.

DETAILED DESCRIPTION OF THE INVENTION

The embodiments of the present application will be described in detail below with reference to the drawings. It is to be understood that the embodiments described herein are merely illustrative and not restrictive.

Any numerical value (including the end values of numerical ranges) provided herein is not limited to the precise value recited, but should be interpreted as covering any value close to said precise value. Moreover, for any numerical range provided herein, one or more new numerical ranges can be obtained by arbitrarily combining the end values of the range, an end value with a specific value provided within the range, or various specific values provided within the range. Such new numerical ranges should also be considered as being specifically disclosed herein.

The RIPP test methods involved in the present application can be found in "Petrochemical Analysis Methods (RIPP Test Methods)", edited by Cuiding YANG et al., Science Press, September 1990, First Edition, pages 263-268, 412-415 and 424-426, ISBN: 7-03-001894-X, which is incorporated herein by reference in its entirety.

All patent and non-patent literatures mentioned herein, including but not limited to textbooks and journal articles, are hereby incorporated by reference in their entirety.

As used herein, the terms "Y-type molecular sieve" and "Y-type zeolite" are used interchangeably, and the terms "NaY molecular sieve" and "NaY zeolite" are also used interchangeably.

As used herein, the term "secondary pores" refers to the pores having a pore size (i.e. pore diameter) of from 2 nm to 100 nm in the molecular sieve.

As used herein, the term "inorganic acid having a medium or higher strength" refers to an inorganic acid having an acid strength not lower than that of $HNO_2$ (nitrous acid), including but not limited to $HClO_4$ (perchloric acid), HI (hydrogen iodide), HBr (hydrobromic acid), HCl (hydrochloric acid), $HNO_3$ (nitric acid), $H_2SeO_4$ (selenic acid), $H_2SO_4$ (sulfuric acid), $HClO_3$ (chloric acid), $H_2SO_3$ (sulfuric acid), $H_3PO_3$ (phosphoric acid), and $HNO_2$ (nitrous acid), and the like.

As used herein, the terms "rare earth solution" and "rare earth salt solution" are used interchangeably, and are preferably an aqueous solution of a rare earth salt.

As used herein, the expression "Y-type molecular sieve having a normal lattice constant" means that the lattice constant of the Y-type molecular sieve is within the range of the lattice constant of conventional NaY molecular sieves, which is preferably in a range of about 2.465 nm to about 2.472 nm.

As used herein, the term "atmospheric pressure" means a pressure of about 1 atm.

As used herein, the weight, on a dry basis, of a material refers to the weight of the solid product obtained after calcining the material at 800° C. for 1 hour.

In a first aspect, the present application provides a catalytic cracking catalyst, comprising, based on the weight of the catalytic cracking catalyst, from about 10% to about 50% by weight, on a dry basis, of a rare earth modified Y-type molecular sieve, about 2% to about 40% by weight, on a dry basis, of an additive-containing alumina and about 10% to about 80% by weight, on a dry basis, of clay; wherein the additive-containing alumina comprises, on a dry basis and based on the weight of the additive-containing alumina, about 60% to about 99.5% by weight of alumina and about 0.5% to about 40% by weight of an additive that is one or more selected from the group consisting of compounds containing alkaline earth metal, lanthanide metal, silicon, gallium, boron and/or phosphorus; the rare earth modified Y-type molecular sieve has a rare earth oxide content of about 4% to about 12% by weight, a phosphorus content of about 0% to about 10% by weight on the basis of $P_2O_5$, a sodium oxide content ($Na_2O$ content) of no more than about 1.0% by weight, preferably no more than about 0.5% by weight, for example, about 0.05% to about 0.5% by weight, a total pore volume of about 0.36 mL/g to about 0.48 mL/g, a percentage of the pore volume of secondary pores having a pore size of 2-100 nm to the total pore volume of the modified Y-type molecular sieve of about 20% to about 40%, a lattice constant of about 2.440 nm to about 2.455 nm, a percentage of the non-framework aluminum content to the total aluminum content of the modified Y-type molecular sieve of no more than about 10%, a lattice collapse temperature of not lower than about 1060° C., and a ratio of B acid to L acid in the total acid content of the modified Y-type molecular sieve of no less than about 3.5, as determined by pyridine adsorption infrared spectroscopy at 200° C.

In a preferred embodiment, in the catalytic cracking catalyst provided in the present application, the rare earth modified Y-type molecular sieve has a lattice collapse temperature of not lower than about 1060° C. Preferably, the molecular sieve has a lattice collapse temperature of about 1060° C. to about 1085° C., for example about 1065° C. to about 1085° C., about 1067° C. to about 1080° C. or about 1064° C. to about 1081° C.

In a preferred embodiment, in the catalytic cracking catalyst provided in the present application, the rare earth modified Y-type molecular sieve has a ratio of B acid to L acid in the total acid content of the modified Y-type molecular sieve of about 3.5 to about 6.0, for example, about 3.5-5.5, about 3.6-5.5, about 3.5-5.0 or about 3.5-4.6, as determined by pyridine adsorption infrared spectroscopy at 200° C.

In a preferred embodiment, in the catalytic cracking catalyst provided in the present application, the rare earth modified Y-type molecular sieve has a lattice constant of about 2.440 nm or about 2.455 nm, for example, 2.442-2.453 nm or 2.442-2.451 nm.

In a preferred embodiment, in the catalytic cracking catalyst provided in the present application, the rare earth modified Y-type molecular sieve is a high-silica Y-type molecular sieve having a framework silica-alumina ratio ($SiO_2/Al_2O_3$ molar ratio) of about 7 to about 14, for example, about 7.8-12.6, about 8.5-12.6, about 8.7-12 or about 9.2-11.4.

In a preferred embodiment, in the catalytic cracking catalyst provided in the present application, the rare earth modified Y-type molecular sieve has a percentage of non-framework aluminum content to the total aluminum content of no more than about 10%, for example from about 5% to about 9.5% by weight or from about 6% to about 9.5% by weight.

In a preferred embodiment, in the catalytic cracking catalyst provided in the present application, the rare earth modified Y-type molecular sieve has a relative crystallinity retention of about 38% or more, for example, about 38-65%, about 38-60%, about 50-60%, about 46-58%, about 46-60% or about 52-60%, after aging for 17 hours at 800° C. under atmospheric pressure in an atmosphere of 100 vol % steam.

In a preferred embodiment, in the catalytic cracking catalyst provided in the present application, the rare earth modified Y-type molecular sieve has a relative crystallinity of no less than about 70%, for example, about 70% to about 80%, particularly about 70-76% or ab out 71-77%.

In a preferred embodiment, in the catalytic cracking catalyst provided in the present application, the rare earth modified Y-type molecular sieve has a specific surface area of about 600 $m^2/g$ to about 680 $m^2/g$, for example, about 600-670 $m^2/g$, about 610-670 $m^2/g$, about 640-670 $m^2/g$ or about 646-667 $m^2/g$.

In a preferred embodiment, in the catalytic cracking catalyst provided in the present application, the rare earth modified Y-type molecular sieve has a total pore volume of about 0.36 mL/g to about 0.48 mL/g, for example, about 0.38-0.45 mL/g, about 0.38-0.42 mL/g, or about 0.4-0.48 mL/g.

In a preferred embodiment, in the catalytic cracking catalyst provided in the present application, the rare earth modified Y-type molecular sieve has a pore volume of secondary pores having a pore size of 2.0 nm to 100 nm of about 0.08 mL/g to about 0.18 mL/g, for example, about 0.1 to about 0.16 mL/g.

In a preferred embodiment, in the catalytic cracking catalyst provided in the present application, the rare earth modified Y-type molecular sieve has a percentage of the pore volume of secondary pores having a pore size of 2.0 nm to 100 nm to the total pore volume of about 20% to about 40%, for example, about 20-38%, about 25-38%, about 28-38% or about 25-35%.

In a further preferred embodiment, the percentage of the total pore volume of secondary pores having a pore size of 8-100 nm to the total pore volume of secondary pores having a pore size of 2-100 nm of the modified Y-type molecular sieve is about 40% to about 80%, for example, about 45-75% or about 55-77%.

In a preferred embodiment, in the catalytic cracking catalyst provided in the present application, the rare earth modified Y-type molecular sieve has a rare earth oxide content, on the basis of $RE_2O_3$, of about 4% to about 12% by weight, for example, about 4% to about 11% by weight or about 5% to about 12% by weight, preferably about 4.5-10% by weight, about 5.5-10% by weight or about 5-9% by weight.

In a preferred embodiment, in the catalytic cracking catalyst provided in the present application, the rare earth modified Y-type molecular sieve comprises phosphorus element, and the modified Y-type molecular sieve has a phosphorus content, on the basis of $P_2O_5$, of about 0.05% to about 10% by weight, preferably 0.1-6 wt %, for example about 1-4% by weight.

In a preferred embodiment, in the catalytic cracking catalyst provided in the present application, the rare earth modified Y-type molecular sieve has a sodium oxide content of no more than about 0.5%, about 0.05% to about 0.5% by weight, for example, about 0.1% to about 0.4% by weight, about 0.05-0.3% by weight or about 0.15-0.3% by weight.

In a preferred embodiment, the catalytic cracking catalyst provided in the present application comprises the rare earth modified Y-type molecular sieve in an amount, on a dry basis, of about 15-45 wt %, for example, about 20-40 wt % or about 25-35 wt %.

In a preferred embodiment, in the catalytic cracking catalyst provided in the present application, the clay is present in an amount of about 10% to about 70% by weight based on the weight of the catalytic cracking catalyst. The clay is one or more selected from the group consisting of the clays suitable for use as a component in cracking catalysts, such as one or more selected from the group consisting of kaolin, hydrated halloysite, montmorillonite, diatomaceous earth, halloysite, saponite, rector, sepiolite, attapulgite, hydrotalcite and bentonite, which are well known to those skilled in the art. Preferably, in the catalytic cracking catalyst provided in the present application, the clay may be present in an amount of about 20-55% by weight or about 30-50% by weight on a dry basis.

In a preferred embodiment, in the catalytic cracking catalyst provided in the present application, the additive-containing alumina is present in an amount of about 2% to about 40% by weight, preferably about 2-20% by weight, based on the weight of the catalytic cracking catalyst. Preferably, the additive-containing alumina can be prepared in accordance with the methods as described in the patent application publication Nos. CN1915486A, CN1915485A, and CN1916116A, all of which are hereby incorporated by reference in entirety. Preferably, the additive-containing alumina comprises 70-95% by weight of alumina and 5-30% by weight of the additive, on a dry basis and based on the weight of the additive-containing alumina. Particularly preferably, the additive is a compound containing phosphorus and/or magnesium.

In a preferred embodiment, the additive-containing alumina is prepared by a method comprising the following steps:

(1) mixing pseudo-boehmite with an amount of water sufficient to make a slurry and acid under stirring, wherein the acid is used in an amount such that the weight ratio of the acid to the alumina in the pseudo-boehmite is about 0.01-0.5;

(2) subjecting the mixed slurry obtained in the step (1) to aging at a temperature of from room temperature to about 90° C. for about 0-24 hours; and (3) mixing the product obtained in step (2) with an additive, optionally drying and optionally calcining.

In a further preferred embodiment, in the step (1) of the method for preparing the additive-containing alumina, the acid is used in an amount such that the weight ratio of the acid to the alumina in the pseudo-boehmite is about 0.05-0.3. Preferably, the pseudo-boehmite and water are slurried in the step (1) to form a slurry having a solid content of from about 10% to about 50% by weight, preferably from about 15% to about 30% by weight. The acid is one or more selected from the group consisting of an inorganic acid and an organic acid. For example, the inorganic acid may be one or more of hydrochloric acid, nitric acid, sulfuric acid, and phosphoric acid, and the organic acid may be one or more of formic acid, acetic acid, oxalic acid and citric acid, preferably hydrochloric acid or nitric acid.

In a further preferred embodiment, in the step (2) of the method for preparing the additive-containing alumina, the aging temperature is from room temperature to about 80° C., the room temperature is, for example, about 15-40° C., and the aging time is about 0.5-4 hours.

In a preferred embodiment, the mixture of the product of the step (2) and the additive obtained in the step (3) of the method for preparing the additive-containing alumina can be directly used for preparing a catalytic cracking catalyst, that is, the formed mixture can be mixed with other components for forming the catalytic cracking catalyst or can be used to prepare a catalyst after drying and calcination. The drying is, for example, oven drying and spray drying.

In a further preferred embodiment, in the step (3) of the method for preparing the additive-containing alumina, the calcination temperature is about 350-800° C., for example about 400-600° C., and the calcination time is, for example, about 0.5-8 hours.

In a preferred embodiment, the additive is one or more selected from the group consisting of compounds containing alkaline earth metal, lanthanide metal, silicon, gallium, boron and/or phosphorus. The compound containing alkaline earth metal, lanthanide metal, silicon, gallium, boron and/or phosphorus may be an oxide or a hydrous oxide of these elements, such as one or more of magnesium oxide and magnesium hydroxide as the alkaline earth metal, rare earth oxide as the lanthanide metal, silica, silica sol, and phosphorus oxide; or salts containing the above elements, such as one or more of nitrates of alkaline earth metals, rare earth chlorides as the lanthanide metal, silicates and phosphates. When the additive is an oxide and/or a hydrous oxide of the elements, the mixing is carried out by directly mixing the product obtained in the step (2) with the additive; when the additive is one or more of the salts containing the elements, the mixing is preferably carried out by first formulating the salt into an aqueous solution and then mixing the solution with the product obtained in the step (2). The mixing involved in each step can be carried out by various existing methods, and the preferred method is to mix under conditions sufficient to slurry the materials (such as pseudo-boehmite, the additive), and the slurrying method is well known to those skilled in the art, which comprises introducing a sufficient amount of water to slurry the material such that the solid content of the slurry is generally from about 10% to about 50% by weight, preferably from about 15% to about 30% by weight.

In a preferred embodiment, the catalytic cracking catalyst according to the present application may further comprise an alumina binder in an amount of no more than about 32% by weight, preferably from about 5% to about 32% by weight, on a dry basis and based on the weight of the catalyst. Preferably, the alumina binder is one or more selected from the group consisting of various forms of alumina, hydrated alumina, and aluminum sol commonly used in cracking catalysts. For example, it can be one or more selected from the group consisting of γ-alumina, η-alumina, θ-alumina, χ-alumina, pseudo-boehmite, boehmite, gibbsite, Bayerite or aluminum sol, preferably pseudo-boehmite and/or aluminum sol. For example, the catalytic cracking catalyst comprises from about 2% to about 15% by weight, preferably from 3% to 10% by weight, on a dry basis, of an aluminum sol binder and/or from about 10% to about 30% by weight, preferably from about 15% to about 25% by weight, on a dry basis, of pseudo-boehmite binder.

In a preferred embodiment, the total content of the alumina binder and the additive-containing alumina in the catalyst according to the present application is from about 10% to about 40% by weight, for example from about 20% to about 35% by weight, and the content of the additive-containing alumina is about 2% to about 20% by weight, based on the weight of the catalyst.

In a preferred embodiment, the catalytic cracking catalyst according to the present application comprises, based on the weight of the catalytic cracking catalyst, about 10% to about 50% by weight, for example, about 15-45% by weight or about 25-40% by weight, on a dry basis, of said rare earth modified Y-type molecular sieve, and about 50% to about 90% by weight, for example about 55-85% by weight or about 60-75% by weight, on a dry basis, of a matrix comprising said additive-containing alumina, clay, and optionally a binder, which is preferably a alumina binder.

In a preferred embodiment, the catalyst provided in the present application may further comprise an additional molecular sieve other than the modified Y-type molecular sieve. The additional molecule sieve can be selected from molecular sieves useful in catalytic cracking catalysts, such as one or more of zeolites having MFI structure, Beta zeolite, other Y zeolites, and non-zeolitic molecular sieves. The additional molecular sieve may be present in an amount, on a dry basis, of about 0% to about 40% by weight, for example from about 0% to about 30% by weight or from about 1% to about 20% by weight. Preferably, the additional Y-type molecular sieve is present in an amount, on a dry basis, of no more than about 40% by weight, for example from about 1% to about 40% by weight or from about 0% to about 20% by weight. The additional Y-type molecular sieve may be, for example, one or more of REY, REHY, DASY, SOY, and PSRY; the zeolite having MFI structure may be, for example, one or more of HZSM-5, ZRP, and ZSP; the beta zeolite may be, for example, HP; and the non-zeolitic molecular sieve may be, for example, one or more of aluminum phosphate molecular sieves (AlPO molecular sieves) and silicoaluminophosphate molecular sieves (SAPO molecular sieves). Preferably, the additional molecular sieve is present in an amount of no more than about 20% by weight, based on the weight of the catalyst.

In a preferred embodiment, the catalytic cracking catalyst provided in the present application comprises, on a dry basis and based on the weight of the catalyst, about 10% to about 50% by weight of the rare earth modified Y-type molecular sieve, about 2% to about 40% by weight of the additive-containing alumina, about 0% to about 40% by weight of the alumina binder, and about 10% to about 80% by weight of the clay. Preferably, the catalytic cracking catalyst comprises, on a dry basis, about 25-40% by weight of the rare earth modified Y-type molecular sieve, about 2-20% by weight of the additive-containing alumina, about 5-30% by weight of the alumina binder and about 30-50% by weight of the clay, and the total content of the alumina binder and the additive-containing alumina is about 20-35% by weight.

In a preferred embodiment, in the catalytic cracking catalyst provided in the present application, the rare earth modified Y-type molecular sieve has a rare earth oxide content of from about 4% to about 12% by weight, for example from about 4% to about 11% by weight, from about 5% to about 12% by weight, from about 4.5% to about 10% by weight or from about 5.5% to about 10% by weight; a phosphorus content, on the basis of $P_2O_5$, of about 0% to about 10% by weight, for example about 0.05% to about 10% by weight, about 0.1% to about 6% by weight or about 0.1% to about 5% by weight; a sodium oxide content of about 0.05% to about 0.5% by weight, for example about 0.1% to about 0.4% by weight or about 0.05% to about 0.3% by weight, preferably less than 0.2% by weight; a total pore volume of about 0.36 mL/g to about 0.48 mL/g, a percentage of the pore volume of secondary pores having a pore size of about 2-100 nm to the total pore volume of about 20% to about 38%, for example, about 28% to about 38% or about 25% to about 35%; a lattice constant of about 2.440 nm to about 2.455 nm, for example, 2.441-2.453 nm, 2.442-2.451 nm or 2.442-2.453 nm; a framework silica-alumina ratio ($SiO_2/Al_2O_3$ molar ratio) of about 7 to about 14, for example about 7.8-12.6, about 8.5-12.6 or about 9.2-11.4; a percentage of non-framework aluminum content to the total aluminum content of the molecular sieve of no more than about 10%, for example about 6-9.5% or about 3-9%; a relative crystallinity of no less than about 60%, for example no less than about 70%, no less than about 71%, or about 70% to about 80%; a lattice collapse temperature of about 1065° C. to about 1080° C.; and a ratio of B acid to L acid in the total acid content of the modified Y-type molecular sieve of no less than about 3.50, for example, about 3.5 to about 6, preferably about 3.5-4.6 or about 3.6-4.6, as determined by pyridine adsorption infrared spectroscopy at 200° C.

In a preferred embodiment, in the catalytic cracking catalyst provided in the present application, the modified Y-type molecular sieve is an ultra-stable rare earth modified Y-type molecular sieve rich in secondary pores, in which the secondary pores having a pore size of 2-100 nm show a dual probable pore size distribution. As shown in FIG. 1, the most probable pore size of secondary pores having a relatively smaller pore size is about 2-5 nm, and the most probable pore size of secondary pores having a relatively larger pore size is about 6-20 nm, for example, about 8-20 nm or about 8-18 nm. Preferably, the percentage of the total pore volume of secondary pores having a pore size of 8 to 100 nm to the total pore volume of secondary pores having a pore size of 2 to 100 nm is about 40-80%, for example, about 45-75%, about 45-77%, about 45-55% or about 55-77%. The modified Y-type molecular sieve has a $SiO_2/Al_2O_3$ ratio of about 7 to about 14, for example about 7.8-13 or about 8.5-12.6, and a lattice constant of about 2.440-2.455 nm, for example 2.441-2.453 nm or 2.442-2.453 nm.

In a preferred embodiment, the preparation of the modified Y-type molecular sieve comprised in the catalytic cracking catalyst provided in the present application comprises the step of contacting the Y-type molecular sieve with silicon tetrachloride for Si—Al isomorphous substitution reaction.

In certain embodiments, the modified Y-type molecular sieve provided in the present application does not show a "surface enrichment of silicon", but shows a ratio of surface $SiO_2/Al_2O_3$ molar ratio to framework $SiO_2/Al_2O_3$ molar ratio of less than or equal to 1, typically less than 1.

In a second aspect, the present application provides a method for the preparation of a catalytic cracking catalyst, comprising the steps of providing a rare earth modified Y-type molecular sieve, forming a slurry comprising the rare earth modified Y-type molecular sieve, an additive-containing alumina, clay, and water, and spray drying, wherein the additive-containing alumina comprises, based on the weight of the additive-containing alumina, 60% to 99.5% by weight of alumina and 0.5% to 40% by weight of an additive that is one or more selected from the group consisting of compounds containing alkaline earth metal, lanthanide metal, silicon, gallium, boron and/or phosphorus; the rare earth modified Y-type molecular sieve has a rare earth oxide content of about 4% to about 12% by weight, a phosphorus content of about 0% to about 10% by weight on the basis of $P_2O_5$, a sodium oxide content of no more than about 1.0% by weight, a total pore volume of about 0.36 mL/g to about 0.48 mL/g, a percentage of the pore volume of secondary pores having a pore size of 2-100 nm to the total pore volume of the modified Y-type molecular sieve of about 20% to about 40%, a lattice constant of about 2.440 nm to about 2.455 nm, a percentage of non-framework aluminum content to the total aluminum content of the modified Y-type molecular sieve of no more than about 10%, a lattice collapse temperature of not lower than about 1060° C., and a ratio of B acid to L acid in the total acid content of the modified Y-type molecular sieve of no less than about 3.5, as determined by pyridine adsorption infrared spectroscopy at 200° C.

In a preferred embodiment, the step of providing a rare earth modified Y-type molecular sieve comprises preparing the rare earth modified Y-type molecular sieve by the following steps:

(1) contacting a NaY molecular sieve with a rare earth salt solution for ion-exchange reaction, to obtain a rare earth modified Y-type molecular sieve having a reduced sodium oxide content;

(2) subjecting the Y-type molecular sieve obtained in the step (1) to roasting at a temperature of about 350° C. to about 520° C. in an atmosphere containing about 30 vol % to about 90 vol % of steam for about 4.5 hours to about 7 hours, to obtain a Y-type molecular sieve having a reduced lattice constant;

(3) contacting and reacting the Y-type molecular sieve obtained in the step (2) with gaseous silicon tetrachloride at a weight ratio of $SiCl_4$ to the Y-type molecular sieve on a dry basis ranging from about 0.1:1 to about 0.7:1 and a reaction temperature of about 200° C. to 650° C. for a reaction time of about 10 minutes to about 5 hours, to obtain a gas phase ultra-stabilized Y-type molecular sieve;

(4) contacting the modified Y-type molecular sieve obtained in the step (3) with an acid solution; and (5) optionally, subjecting the acid-treated molecular sieve obtained in the step (4) to phosphorus modification by contacting with a phosphorus compound.

In a preferred embodiment, the method for the preparation of a catalytic cracking catalyst provided in the present application comprises the steps of preparing a rare earth modified Y-type molecular sieve, forming a slurry comprising the rare earth modified Y-type molecular sieve, an additive-containing alumina, clay, water, and optionally an alumina binder, and spray drying, wherein said preparing a rare earth modified Y-type molecular sieve further comprises the steps of:

(1) contacting a NaY molecular sieve with a rare earth solution for ion-exchange reaction, filtering and washing to obtain a rare earth modified Y-type molecular sieve having a normal lattice constant and a reduced sodium oxide content;

(2) subjecting the rare earth modified Y-type molecular sieve having a normal lattice constant and a reduced sodium oxide content to motification, and optionally drying, to obtain a Y-type molecular sieve having a reduced lattice constant, wherein the modification comprises subjecting the rare earth modified Y-type molecular sieve having a normal lattice constant and a reduced sodium oxide content to roasting at a temperature of about 350-520° C. or about 350-480° C. in an atmosphere containing about 30 vol % to about 90 vol % of steam (also called 30-90 vol % steam atmosphere or 30-90 vol % steam) for about 4.5 hours to about 7 hours;

(3) contacting the Y-type molecular sieve having a reduced lattice constant with gaseous $SiCl_4$, preferably, at a temperature of about 200 to 650° C. and a weight ratio of $SiCl_4$ to the Y-type molecular sieve having a reduced lattice constant obtained in the step (2) on a dry basis of about 0.1:1 to about 0.7:1 for a reaction time of about 10 minutes to about 5 hours, then washing and filtering, to obtain a gas phase ultra-stabilized Y-type molecular sieve;

(4) subjecting the gas phase ultra-stabilized Y-type molecular sieve obtained in the step (3) to modification by contacting with an acid solution to obtain an acid-treated modified Y-type molecular sieve; and (5) optionally, subjecting the acid-treated modified Y-type molecular sieve obtained in the step (4) to phosphorus modification by contacting with a phosphorus compound.

In some preferred embodiments, in the step (1) of the method for preparing the rare earth modified Y-type molecular sieve comprised in the catalytic cracking catalyst provided in the present application, an ion-exchange reaction between a NaY molecular sieve and a rare earth solution is conducted to obtain a rare earth modified Y-type molecular sieve having a normal lattice constant and a reduced sodium oxide content. The NaY molecular sieve is either commercially available or prepared according to existing methods. In a preferred embodiment, the NaY molecular sieve has a lattice constant of about 2.465-2.472 nm, a framework silica-alumina ratio ($SiO_2/Al_2O_3$ molar ratio) of about 4.5-5.2, a relative crystallinity of about 85% or more, for example, about 85-95%, and a sodium oxide content of about 13.0-13.8 wt %.

In a preferred embodiment, the NaY molecular sieve is subjected to an ion-exchange reaction with a rare earth solution in the step (1) at an ion-exchange temperature of preferably about 15-95° C., for example, about 20-65° C. or about 65-95° C.; for an ion-exchange time of preferably about 30-120 minutes, for example about 45-90 minutes; at a weight ratio of NaY molecular sieve (on a dry basis):rare earth salt (on the basis of $RE_2O_3$):$H_2O$ of about 1:0.01-0.18:5-20.

In a preferred embodiment, the NaY molecular sieve is subjected to an ion-exchange reaction with the rare earth solution by mixing the NaY molecular sieve, the rare earth salt and water at a weight ratio of the NaY molecular sieve:the rare earth salt:$H_2O$ of about 1:0.01-0.18:5-15 to form a mixture, and stirring at a temperature of about 15-95° C., for example, from room temperature to about 60° C., about 65-95° C., about 20-60° C. or about 30-45° C., preferably for about 30-120 minutes to conduct an exchange between rare earth ions and sodium ions.

In a preferred embodiment, the weight ratio of the NaY molecular sieve to water is from about 1:6 to about 1:20, preferably from about 1:7 to about 1:15. The mixture of the NaY molecular sieve, the rare earth salt and water can be formed by mixing the NaY molecular sieve and water to form a slurry, and then adding to the slurry the rare earth salt and/or an aqueous solution of the rare earth salt. The rare earth solution can be a solution of the rare earth salt. The rare earth salt is preferably a rare earth chloride and/or a rare earth nitrate. The rare earth is, for example, one or more of La, Ce, Pr, Nd and mixed rare earths. Preferably, the mixed rare earth comprises one or more of La, Ce, Pr and Nd, or further comprises at least one of rare earths other than La, Ce, Pr, and Nd.

In a preferred embodiment, step (1) further comprises a washing step for the purpose of washing away the exchanged sodium ions, for example, using deionized water or decationized water.

In a preferred embodiment, the rare earth modified Y-type molecular sieve having a normal lattice constant and a reduced sodium oxide content obtained in the step (1) has a rare earth content, on the basis of $RE_2O_3$, of about 4.5-13% by weight, about 5.5-14% by weight, about 7-14% by weight, about 7.5-13% by weight, about 5.5-13% by weight or about 5.5-12% by weight, a sodium oxide content of no more than about 9.5% by weight, for example about 5.5-9.5% by weight, about 5.5-8.5% by weight or about 5.5-7.5% by weight, and a lattice constant of about 2.465-2.472 nm.

In certain preferred embodiments, in the step (2) of the method for preparing the rare earth modified Y-type molecular sieve comprised in the catalytic cracking catalyst provided in the present application, the rare earth modified Y-type molecular sieve having a normal lattice constant is subjected to a treatment at a temperature of about 350° C. to about 520° C., for example about 350-480° C., in an atmosphere containing about 30% to about 90% by volume of steam, for example, about 35% to about 85% by volume of steam, for about 4.5-7 hours.

In a preferred embodiment, in the step (2), the roasting temperature is about 380-460° C., the roasting atmosphere contains about 40-80 vol % of steam, and the roasting time is about 5-6 hours.

In a preferred embodiment, the steam atmosphere contains from about 30% to about 90% by volume of steam, and further comprises other gas(es), such as one or more of air, helium or nitrogen.

In a preferred embodiment, the Y-type molecular sieve having a reduced lattice constant obtained in the step (2) has a lattice constant of about 2.450 nm to about 2.462 nm.

In a preferred embodiment, the Y-type molecular sieve obtained in the step (2) has a water content of no more than about 1% by weight, which is directly used in the reaction of the step (3).

In another preferred embodiment, the step (2) further comprises the step of drying the roasted Y-type molecular sieve to obtain a water content of no more than about 1% by weight.

In a preferred embodiment, the Y-type molecular sieve having a reduced lattice constant obtained in the step (2) has a solid content of no less than about 99% by weight.

In some preferred embodiments, in the step (3) of the method for preparing the rare earth modified Y-type molecular sieve comprised in the catalytic cracking catalyst provided in the present application, the weight ratio of $SiC_4$ to the Y-type molecular sieve (on a dry basis) is preferably about 0.3-0.6:1, and the reaction temperature is preferably from about 350° C. to about 500° C.

In a preferred embodiment, the step (3) may further comprise a washing step, which may be carried out by a conventional washing method, using water such as deionized water or decationized water, for the purpose of removing soluble by-products such as $Na^+$, $Cl^-$, $Al^{3+}$ and the like remaining in the molecular sieve. For example, the washing conditions may include: a weight ratio of the washing water to the molecular sieve of about 5-20:1, usually a weight ratio of the molecular sieve:$H_2O$ of about 1:6-15, a pH of preferably about 2.5-5.0, and a washing temperature of about 30-60° C. Preferably, the washing is carried out to the extent that no free ions like $Na^+$, $Cl^-$ and $Al^{3+}$ can be detected in the spent washing liquid, and the content of each of the $Na^+$, $Cl^-$ and $Al^{3+}$ ions in the molecular sieve after washing is not more than about 0.05% by weight.

In some preferred embodiments, in the step (4) of the method for preparing the rare earth modified Y-type molecular sieve comprised in the catalytic cracking catalyst provided in the present application, the gas phase ultra-stabilized Y-type molecular sieve obtained in the step (3) is contacted and reacted with an acid solution (which is referred to hereinafter as channel cleaning modification, or channel cleaning for short, or referred to as acid treatment modification).

In a preferred embodiment, said contacting and reacting the gas phase ultra-stabilized Y-type molecular sieve obtained in the step (3) with an acid solution is carried out by mixing the molecular sieve treated by gas phase ultra-stablization modification, i.e. the gas phase ultra-stablized Y-type molecular sieve, with the acid solution and reacting for a period of time, and then separating the molecular sieve after the reaction from the acid solution, for example, by filtration, and subjecting it optionally to washing (which is used to remove soluble by-products, such as $Na^+$, $Cl^-$, $Al^{3+}$, and the like, remaining in the molecular sieve, for example, under the following washing conditions: a weight ratio of the washing water to the molecular sieve of about 5-20:1, usually a weight ratio of the molecular sieve:$H_2O$ of about 1:6-15, a pH of preferably about 2.5-5.0, and a washing temperature of about 30-60° C.) and optionally to drying, to obtain the modified Y-type molecular sieve provided in the present application.

In a preferred embodiment, the gas phase ultra-stabilized Y-type molecular sieve obtained in the step (3) is contacted with the acid solution at a weight ratio of the acid to the molecular sieve (on a dry basis) of about 0.001-0.15:1, for example about 0.002-0.1:1 or 0.01-0.05:1, a weight ratio of water to the molecular sieve on a dry basis of about 5-20:1, for example about 8-15:1, and a reaction temperature of about 60-100° C., for example 80-99° C., preferably 88-98° C.

In a preferred embodiment, the acid in the acid solution (an aqueous acid solution) is at least one organic acid and at least one inorganic acid having a medium or higher strength. The organic acid may be one or more of oxalic acid, malonic acid, butanedioic acid (succinic acid), methyl succinic acid, malic acid, tartaric acid, citric acid, and salicylic acid. The inorganic acid having a medium or higher strength may be one or more of phosphoric acid, hydrochloric acid, nitric acid, and sulfuric acid.

In a preferred embodiment, the channel cleaning modification is carried out at a temperature of about 80-99° C., for example about 85-98° C., for a period of about 60 minutes or more, for example about 60-240 minutes or about 90-180 minutes. The weight ratio of the organic acid to the molecular sieve is about 0.01-0.10:1, for example, about 0.03-0.1:1 or 0.02-0.05:1; the weight ratio of the inorganic acid having a medium or higher strength to the molecular sieve is about 0.01-0.06:1, for example about 0.01-0.05:1 or 0.02-0.05:1, and the weight ratio of water to the molecular sieve is preferably from about 5:1 to about 20:1, for example from about 8:1 to about 15:1.

In a preferred embodiment, the channel cleaning modification is carried out in two stages, in which the molecular sieve is firstly contacted with an inorganic acid having a medium or higher strength, wherein the weight ratio of the inorganic acid having a medium or higher strength to the molecular sieve is about 0.01-0.06:1, for example about 0.02-0.05:1, the weight ratio of water to the molecular sieve is preferably about 5-20:1, for example about 8-15:1, the reaction temperature is about 80-99° C., preferably 90-98° C., and the reaction time is about 60-120 minutes; and then the molecular sieve obtained after the treatment is contacted with an organic acid, wherein the weight ratio of the organic acid to the molecular sieve is about 0.02-0.1:1, for example, about 0.02-0.10:1 or 0.05-0.08:1, the weight ratio of water to the molecular sieve is preferably from about 5:1 to about 20:1, for example from about 8:1 to about 15:1, the reaction temperature is from about 80° C. to about 99° C., preferably from about 90° C. to about 98° C., and the reaction time is about 60 to 120 minutes, wherein the weight ratio is calculated using the weight of the molecular sieve on a dry basis.

In some preferred embodiments, in the method for preparing the rare earth modified Y-type molecular sieve comprised in the catalytic cracking catalyst provided in the present application, the acid-treated modified Y-type molecular sieve obtained in the step (4) is subjected to phosphorus modification in the step (5) to introduce phosphorus into the molecular sieve. The phosphorus modification generally comprises contacting the acid-treated modified Y-type molecular sieve obtained in the step (4) with an exchange liquid containing a phosphorus compound typically at 15-100° C., preferably at 30-95° C., for 10-100 minutes, then filtering, and optionally washing. The weight ratio of water in the exchange liquid to the molecular sieve is from about 2 to about 5, preferably from 3 to 4, and the weight ratio of phosphorus (calculated on the basis of $P_2O_5$) to the molecular sieve is from about 0.0005 to about 0.10, preferably from 0.001 to 0.06. The phosphorus compound may be one or more selected from the group consisting of phosphoric acid, ammonium phosphate, ammonium dihydrogen phosphate, and diammonium hydrogen phosphate. The washing can be carried out, for example, with water, such as decationized or deionized water, in amount of 5-15 times the weight of the molecular sieve.

In a preferred embodiment, the phosphorus modification can be carried out by the following: adding the acid-treated modified Y-type molecular sieve to an exchange liquid containing a phosphorus compound to conduct an ion-exchange reaction at about 15-100° C. for about 10-100 minutes, then filtering and washing; wherein in the mixture formed by the exchange liquid containing the phosphorus compound and the molecular sieve, the weight ratio of water to the molecular sieve is about 2-5, preferably about 3-4, and the weight ratio of phosphorus (calculated on the basis of $P_2O_5$) to the molecular sieve is from about 0.0005 to about 0.10, preferably from about 0.001 to about 0.06.

In a preferred embodiment, the present application provides a method for the preparation of a catalytic cracking catalyst, comprising the steps of preparing a rare earth modified Y-type molecular sieve, mixing the rare earth modified Y-type molecular sieve, an alumina binder, a clay, and water to form a slurry, spray drying, and optionally washing and drying, wherein said preparing the rare earth modified Y-type molecular sieve comprises the following steps:

(1) subjecting the NaY molecular sieve to an ion-exchange reaction with a rare earth solution, filtering and washing to obtain a rare earth modified Y-type molecular sieve having a normal lattice constant and a reduced sodium oxide content, wherein the ion-exchange is carried out at a temperature of about 15-95° C., preferably about 65-95° C., for about 30-120 minutes under stirring;

(2) subjecting the Y-type molecular sieve obtained in the step (1) to roasting in an atmosphere containing about 30% to about 90% by volume of steam at a temperature of about 350-480° C. for about 4.5 hours to about 7 hours, and drying to obtain a Y-type molecular sieve having a reduced lattice constant and a water content of less than about 1% by weight, wherein the lattice constant of the Y-type molecular sieve having a reduced lattice constant is about 2.450-2.462 nm;

(3) contacting and reacting the Y-type molecular sieve obtained in the step (2) with a gaseous $SiCl_4$ vaporized by heat at a weight ratio of $SiCl_4$ to the Y-type molecular sieve (on a dry basis) of about 0.1:1 to about 0.7:1 and a temperature of about 200-650° C. for about 10 minutes to about 5 hours, optionally washing and filtering, to obtain a gas phase ultra-stablilized modified Y-type molecular sieve;

(4) subjecting the gas phase ultra-stablilized modified Y-type molecular sieve obtained in the step (3) to an acid treatment modification, wherein the gas phase ultra-stablilized modified Y-type molecular sieve obtained in the step (3) is firstly mixed and contacted with an inorganic acid having a medium or higher strength and water at about 80-99° C., preferably about 90-98° C., for at least about 30 minutes, for example about 60-120 minutes, and then an organic acid is added and further contacted at about 80-99° C., preferably about 90-98° C., for at least about 30 minutes, for example about 60-120 minutes, and the resultant is subjected to filtration, optionally to washing, and optionally to drying, to obtain an acid-treated modified Y-type molecular sieve, wherein preferably, the weight ratio of the organic acid to the molecular sieve on a dry basis is about 0.02-0.10:1, the weight ratio of the inorganic acid having a medium or higher strength to the molecular sieve on a dry basis is about 0.01-0.05:1, and the weight ratio of water to the molecular sieve is about 5-20:1, and (5) optionally, adding the acid-treated modified Y-type molecular sieve to an exchange liquid containing a phosphorus compound to conduct an ion-exchange reaction at about 15-100° C. for about 10-100 minutes, filtering, washing, and optionally drying, wherein the weight ratio of water in the exchange liquid to the molecular sieve is about 2-5, preferably about 3-4, and the weight ratio of phosphorus (calculated on the basis of $P_2O_5$) to the molecular sieve is about 0.005-0.10, preferably about 0.01-0.05.

In the method for the preparation of the catalyst according to the present application, all steps except for the step of providing or preparing the rare earth modified Y-type molecular sieve, can be carried out in accordance with existing methods, which are described in detail in the patent application publication Nos. CN1916116A, CN1362472A, CN1727442A, CN1132898C, CN1727445A and CN1098130A, which are incorporated herein by reference. Further, said spray drying, washing, and drying are conventional technical means, and the present application has no special requirements. For example, in a preferred embodiment, the method for the preparation of the catalyst comprises the steps of mixing the modified Y-type molecular sieve, the additive-containing alumina, the clay, the optional alumina binder, and water to form a slurry, spray drying, washing, filtering, and drying.

Particularly preferably, the present application provides the following preferred embodiments:

Item 1. A catalytic cracking catalyst, comprising from about 10% to about 50% by weight on a dry basis of a rare earth modified Y-type molecular sieve, from about 2% to about 40% by weight on a dry basis of an additive-containing alumina, and about 10% to about 80% by weight on a dry basis of clay; wherein on a dry basis, the additive-containing alumina comprises about 60% to about 99.5% by weight of alumina and about 0.5% to about 40% by weight of an additive that is one or more selected from the group consisting of compounds containing alkaline earth metal, lanthanide metal, silicon, gallium, boron or phosphorus; the rare earth modified Y-type molecular sieve has a rare earth oxide content of about 4% to about 12% by weight, a phosphorus content on the basis of $P_2O_5$ of about 0% to about 10% by weight, a sodium oxide content of no more than about 0.5% by weight, a total pore volume of about 0.36 mL/g to about 0.48 mL/g, a percentage of the pore volume of secondary pores having a pore size of 2-100 nm to the total pore volume of the modified Y-type molecular sieve of about 20% to about 40%, a lattice constant of about 2.440 nm to about 2.455 nm, a percentage of non-framework aluminum content to the total aluminum content of the modified Y-type molecular sieve of no more than about 10%, a lattice collapse temperature of not lower than about 1060° C., and a ratio of B acid to L acid in the total acid content of the rare earth modified Y-type molecular sieve of no less than about 3.5, as determined by pyridine adsorption infrared spectroscopy at 200° C.

Item 2. A catalytic cracking catalyst, comprising about 10% to about 50% by weight on a dry basis of a rare earth modified Y-type molecular sieve, about 2% to about 40% by weight on a dry basis of an additive-containing alumina, and about 10% to about 80% by weight on a dry basis of clay; wherein on a dry basis, the additive-containing alumina comprises about 60% to about 99.5% by weight of alumina and about 0.5% to about 40% by weight of an additive that is one or more selected from the group consisting of compounds containing alkaline earth metal, lanthanide metal, silicon, gallium, boron or phosphorus; the modified Y-type molecular sieve has a rare earth oxide content of about 5% to about 12% by weight, a sodium oxide content of no more than about 0.5% by weight, a total pore volume of about 0.36 mL/g to about 0.48 mL/g, a percentage of the pore volume of secondary pores having a pore size of 2-100 nm to the total pore volume of about 20%-38%, a lattice constant of about 2.440 nm to about 2.455 nm, a percentage of non-framework aluminum content to the total aluminum content of the modified Y-type molecular sieve of no more than about 10%, a lattice collapse temperature of not lower than about 1060° C., and a ratio of B acid to L acid in the total acid content of the rare earth modified Y-type molecular sieve of no less than about 3.5, as determined by pyridine adsorption infrared spectroscopy at 200° C.

Item 3. A catalytic cracking catalyst, comprising from about 10% to about 50% by weight on a dry basis of a rare earth modified Y-type molecular sieve, from about 2% to about 40% by weight on a dry basis of an additive-containing alumina, and about 10% to about 80% by weight on a dry basis of clay; wherein on a dry basis, the additive-containing alumina comprises about 60% to about 99.5% by weight of alumina and about 0.5% to about 40% by weight of an additive that is one or more selected from the group consisting of compounds containing alkaline earth metal, lanthanide metal, silicon, gallium, boron or phosphorus; the rare earth modified Y-type molecular sieve has a rare earth oxide content of about 4% to about 11% by weight, a phosphorus content on the basis of $P_2O_5$ of about 0.5-10% by weight, a sodium oxide content of no more than about 0.5% by weight, a total pore volume of about 0.36 mL/g to about 0.48 mL/g, a percentage of the pore volume of secondary pores having a pore size of 2-100 nm to the total pore volume of the modified Y-type molecular sieve of about 20% to about 40%, a lattice constant of about 2.440 nm to about 2.455 nm, a percentage of non-framework aluminum content to the total aluminum content of the modified Y-type molecular sieve of no more than about 10%, a lattice collapse temperature of not lower than about 1060° C., and a ratio of B acid to L acid in the total acid content of the rare earth modified Y-type molecular sieve of no less than about 3.5, as determined by pyridine adsorption infrared spectroscopy at 200° C.

Item 4. The catalytic cracking catalyst according to any one of the above items, wherein the percentage of the pore volume of secondary pores having a pore size of 2-100 nm to the total pore volume of the rare earth modified Y-type molecular sieve is about 28-38%.

Item 5. The catalytic cracking catalyst according to any one of items 1 to 4, wherein the percentage of the non-framework aluminum content to the total aluminum content of the rare earth modified Y-type molecular sieve is about 5% to about 9.5% by weight, and the framework silica-alumina ratio in terms of the $SiO_2/Al_2O_3$ molar ratio is about 7 to about 14.

Item 6. The catalytic cracking catalyst according to any one of Items 1 to 5, wherein the rare earth modified Y-type molecular sieve has a lattice collapse temperature of about 1060° C. to about 1085° C.

Item 7. The catalytic cracking catalyst according to any one of Items 1 to 6, characterized in that the ratio of B acid to L acid in the total acid content of the rare earth modified Y-type molecular sieve is about 3.5 to about 6, as determined by pyridine adsorption infrared spectroscopy at 200° C.

Item 8. The catalytic cracking catalyst according to any one of Items 1 to 7, wherein, after aging at 800° C. under atmospheric pressure in 100% steam atmosphere for 17 hours, the rare earth modified Y-type molecular sieve shows a relative crystallinity retention of about 38% or more, for example, about 38-60% or about 50-60%.

Item 9. The catalytic cracking catalyst according to any one of the preceding items, wherein the rare earth modified Y-type molecular sieve has a relative crystallinity of about 70% to about 80%.

Item 10. The catalytic cracking catalyst according to any one of Items 1-9, wherein the rare earth modified Y-type molecular sieve has a rare earth oxide content of about 4.5% to about 10% by weight, a phosphorus content on the basis of $P_2O_5$ of about 0.1-6 wt %, a sodium oxide content of about 0.05-0.3 wt %, a lattice constant of 2.442-2.451 nm, a framework silica-alumina ratio of about 8.5-12.6; or the modified Y-type molecular sieve has a rare earth oxide content of about 5.5-10% by weight, a sodium oxide content of about 0.15-0.3% by weight, a lattice constant of 2.442-2.453 nm, and a framework silica-alumina ratio of about 7.8-12.6.

Item 11. The catalytic cracking catalyst according to any one of Items 1 to 10, wherein a percentage of the total pore volume of secondary pores having a pore size of 8-100 nm to the total pore volume of secondary pores having a pore size of 2-100 nm of the rare earth modified Y-type molecular sieve is about 40-80%.

Item 12. The catalytic cracking catalyst according to any one of Items 1-11, wherein the catalyst comprises about 25-40% by weight on a dry basis of the rare earth modified Y-type molecular sieve, about 2-20% by weight on a dry basis of the additive-containing alumina, about 5-30% by weight on a dry basis of the alumina binder, and about 30-50% by weight on a dry basis of the clay.

Item 13. The catalytic cracking catalyst according to any one of Items 1 to 12, wherein the clay is one or more selected from the group consisting of kaolin, hydrated halloysite, montmorillonite, diatomaceous earth, halloysite, saponite, rector, sepiolite, attapulgite, hydrotalcite and bentonite.

Item 14. The catalytic cracking catalyst according to any one of the preceding items, wherein the additive-containing alumina is obtained by the following steps:

(1) mixing pseudo-boehmite with an amount of water sufficient to make a slurry and acid under stirring, wherein the acid is used in an amount such that the weight ratio of the acid to the alumina in the pseudo-boehmite is about 0.01-0.5;

(2) subjecting the mixed slurry obtained in the step (1) to aging at a temperature of from room temperature to about 90° C. for about 0 to 24 hours; and (3) mixing the product obtained in the step (2) with an additive, optionally drying and optionally calcining.

Item 15. A method for the preparation of a catalytic cracking catalyst, comprising the steps of preparing a rare earth modified Y-type molecular sieve, forming a slurry comprising the rare earth modified Y-type molecular sieve, an additive-containing alumina, clay, and water, and spray-drying, wherein, based on the weight of the additive-containing alumina, the additive-containing alumina comprises about 60% to about 99.5% by weight of alumina and about 0.5% to about 40% by weight of an additive that is one more more selected from the group consisting of compounds containing alkaline earth metal, lanthanide metal, silicon, gallium, boron or phosphorus; said preparing the rare earth modified Y-type molecular sieve comprises the following steps:

(1) contacting a NaY molecular sieve with a rare earth salt solution for ion-exchange reaction, filtering, washing, and optionally drying to obtain a rare earth modified Y-type molecular sieve having a normal lattice constant and a reduced sodium oxide content;

(2) subjecting the above-mentioned rare earth modified Y-type molecular sieve having a normal lattice constant and a reduced sodium oxide content to roasting at a temperature of about 350-520° C., preferably 350-480° C. in an atmosphere containing 30-90 vol % of steam for about 4.5-7 hours, and optionally drying, to obtain a Y-type molecular sieve having a reduced lattice constant;

(3) contacting and reacting the Y-type molecular sieve having a reduced lattice constant with gaseous silicon tetrachloride at a weight ratio of $SiCl_4$ to the Y-type molecular sieve having a reduced lattice constant on a dry basis of about 0.1:1 to about 0.7:1, and a reaction temperature of about 200-650° C., for a period of about 10 minutes to about 5 hours, optionally washing and filtering to obtain a gas phase ultra-stabilized Y-type molecular sieve;

(4) contacting the gas phase ultra-stabilized Y-type molecular sieve obtained in the step (3) with an acid solution; and (5) optionally, subjecting the molecular sieve obtained by contacting with the acid solution in the step (4) to phosphorus modification by contacting with a phosphorus compound.

Item 16. The method according to Item 15, wherein the rare earth modified Y-type molecular sieve having a normal lattice constant and a reduced sodium oxide content obtained in the step (1) has a lattice constant of 2.465-2.472 nm, and a sodium oxide content of no more than about 9.0% by weight.

Item 17. The method of item 15, wherein the rare earth modified Y-type molecular sieve having a normal lattice constant and a reduced sodium oxide content obtained in the step (1) has a rare earth content of about 4.5-13% by weight on the basis of $RE_2O_3$, a sodium oxide content of about 4.5-9.5 wt %, for example about 5.5-8.5 wt %, and a lattice constant of about 2.465-2.472 nm.

Item 18. The method according to any one of Items 15-17, characterized in that, in the step (1), said contacting the NaY molecular sieve with the rare earth salt solution for ion-exchange reaction is carried out by forming a mixture of NaY molecular sieve, rare earth salt and water at a weight ratio of the NaY molecular sieve:rare earth salt:$H_2O$ of about 1:0.01-0.18:5-20, and stirring.

Item 19. The method according to any one of Items 15-18, characterized in that, in the step (1), said contacting the NaY molecular sieve with the rare earth solution for ion-exchange reaction comprises: mixing the NaY molecular sieve with decationized water, adding a rare earth salt and/or a rare earth salt solution with stirring for ion-exchange reaction, filtering, and washing; wherein the conditions for the ion-exchange reaction include: an ion-exchange temperature of about 15-95° C., an ion-exchange time of about 30-120 minutes, and an aqueous rare earth salt solution used as the rare earth salt solution.

Item 20. The method according to any one of Items 15 to 19, wherein the rare earth salt is rare earth chloride or rare earth nitrate, and the phosphorus compound is one or more selected from the group consisting of phosphoric acid, ammonium phosphate, ammonium dihydrogen phosphate and diammonium hydrogen phosphate.

Item 21. The method according to any one of Items 15-20, wherein, in the step (2), the roasting temperature is about 380-480° C. or about 380-460° C., the roasting atmosphere is an atmosphere containing about 40-80 vol % steam, and the roasting time is about 5-6 hours.

Item 22. The method according to any one of Items 15-21, wherein the Y-type molecular sieve having a reduced lattice constant obtained in the step (2) has a lattice constant of 2.450-2.462 nm and a water content of no more than about 1% by weight.

Item 23. The method according to any one of Items 15-22, wherein the washing in the step (3) is carried out using water under the following conditions: a ratio of molecular sieve:H$_2$O of about 1:6-15, a pH value of about 2.5-5.0 and a washing temperature of about 30-60° C.

Item 24. The method according to any one of Items 15-23, characterized in that, in the step (4), said contacting the gas phase ultra-stabilized Y-type molecular sieve obtained in the step (3) with the acid solution is carried out under the following conditions: a weight ratio of acid to the molecular sieve of about 0.001-0.15:1, a weight ratio of water to the molecular sieve of about 5-20:1, an acid that is one or more of organic acids and inorganic acids, a contact time of about 60 minutes or more, preferably about 1-4 hours, and a contact temperature of about 80-99° C.

Item 25. The method according to any one of Items 15-24, wherein the acid solution used in the step (4) comprises an organic acid and an inorganic acid having a medium or higher strength, wherein the weight ratio of the inorganic acid having a medium or higher strength to the molecular sieve is about 0.01-0.05:1, the weight ratio of the organic acid to the molecular sieve is about 0.02-0.10:1, the weight ratio of water to the molecular sieve is about 5-20:1, and the contact temperature is about 80-99° C., and the contact time is about 1-4 hours.

Item 26. The method according to any one of Items 15-25, wherein, in the step (4), the contacting with the acid solution is carried out by first contacting with the inorganic acid having a medium or higher strength, and then contacting with the organic acid, wherein the contacting with the inorganic acid having a medium or higher strength is carried out under the following conditions: a weight ratio of the inorganic acid to the molecular sieve of about 0.01-0.05:1, a weight ratio of water to the molecular sieve of about 5-20:1, a contact time of about 60-120 minutes, and a contact temperature of about 90-98° C.; and the contacting with the organic acid is carried out under the following conditions: a weight ratio of the organic acid to the molecular sieve of about 0.02-0.10:1, a weight ratio of water to the molecular sieve of about 5-20:1, a contact time of about 60-120 minutes, and a contact temperature of about 90-98° C.

Item 27. The method according to any one of Items 24-26, wherein the organic acid is one or more selected from the group consisting of oxalic acid, malonic acid, succinic acid, methyl succinic acid, malic acid, tartaric acid, citric acid and salicylic acid; the inorganic acid having a medium or higher strength is one or more selected from the group consisting of phosphoric acid, hydrochloric acid, nitric acid and sulfuric acid.

Item 28. The method according to any one of Items 15 to 27, wherein, in the step (5), the phosphorus modification is carried out by: contacting the molecular sieve obtained by contacting with the acid solution in the step (4) with the exchange liquid containing a phosphorus compound to conduct an ion-exchange reaction at about 15-100° C. for about 10-100 minutes, filtering, and washing; wherein, in the mixture formed by contacting the exchange liquid with the molecular sieve, the weight ratio of water to the molecular sieve is about 2-5, preferably about 3-4, and the weight ratio of phosphorus (calculated on the basis of P$_2$O$_5$) to the molecular sieve is from about 0.0005 to about 0.10, preferably from about 0.001 to about 0.06.

EXAMPLES

The present application will be further illustrated by the following examples, without however limiting the present invention.

Feedstocks: In the following examples and comparative examples, NaY molecular sieves are supplied by Qilu Branch of Sinopec Catalyst Co., Ltd., of which the sodium oxide content is 13.5% by weight, the framework silica-alumina ratio (SiO$_2$/Al$_2$O$_3$ molar ratio) is 4.6, the lattice constant is 2.470 nm, and the relative crystallinity is 90%; rare earth chloride and rare earth nitrate are chemically pure reagents Beijing Chemical Plant; pseudo-boehmite is an industrial product Shandong Aluminum Plant with a solid content of 61% by weight; kaolin is China Kaolin Clay Co., Ltd. of Suzhou with a solid content of 76% by weight; aluminum sol is supplied by Qilu Branch of Sinopec Catalyst Co., Ltd. having an alumina content of 21% by weight.

Analytical method: In each of the comparative examples and examples, the element content of the molecular sieve was determined by X-ray fluorescence spectrometry; the lattice constant and relative crystallinity of the molecular sieve were determined by X-ray powder diffraction (XRD) according to the RIPP 145-90, RIPP 146-90 standard method (see "Petrochemical Analysis Methods (RIPP Test Methods)", edited by Cuiding YANG et al., Science Press, September 1990, First Edition, pp. 412-415), the framework silica-alumina ratio of the molecular sieve was calculated according to the following equation:

$$SiO_2/Al_2O_3=(2.5858-a_0)\times 2/(a_0-2.4191)$$

wherein $a_0$ refers to the lattice constant of which the unit is nm.

The total silica-alumina ratio of the molecular sieve was calculated based on the content of Si and Al elements determined by X-ray fluorescence spectrometry. The percentage of the framework Al content to the total Al content was calculated based on the framework silica-alumina ratio determined by XRD and the total silica-alumina ratio determined by XRF, and then the percentage of non-framework Al content to the total Al content was calculated. The lattice collapse temperature was determined by differential thermal analysis (DTA).

In each of the comparative examples and examples, the acid center type of the molecular sieve and the acid content thereof were determined by pyridine adsorption infrared spectroscopy. The instrument was IFS113V type FT-IR (Fourier transform infrared) spectrometer of Bruker Company, USA. The method for determining B acid content and L acid content in the total acid content by pyridine adsorption infrared spectroscopy at 200° C. was as follows: a self-supported sample tablet was placed in an in-situ cell of an infrared spectrometer and sealed; the sample was heated to a temperature of 400° C., vacuumed to 10$^{-3}$ Pa, and maintained at the temperature for 2 h to remove the gas molecules adsorbed by the sample; the sample was cooled to room temperature, a pyridine vapor at a pressure of 2.67 Pa was introduced, and the sample was maintained under such conditions for 30 min to achieve an adsorption equilibrium; then the sample was heated to a temperature of 200° C., and vacuumed to 10$^{-3}$ Pa for desorption for 30 min; after that, the sample was cooled to room temperature and subjected to spectrographic analysis at a scanning wave number range of 1400 cm$^{-1}$ to 1700 cm$^{-1}$, and the pyridine adsorption infrared spectrum of the sample desorbed at 200° C. was obtained. The relative amount of the total Brönsted acid center (B acid center) and the Lewis acid center (L acid center) in the molecular sieve was obtained based on the intensity of the characteristic adsorption peaks at 1540 cm$^{-1}$ and 1450 cm$^{-1}$ in the pyridine adsorption infrared spectrum.

In each of the comparative examples and examples, the method for determining the pore volume of secondary pores was as follows: according to the RIPP 151-90 standard method (see "Petrochemical Analysis Methods (RIPP Test Methods)", Cuiding YANG et al., Science Press, September 1990, First Edition, pp. 424-426), the total pore volume of the molecular sieve was determined based on the adsorption isotherm, and then the micropore volume of the molecular sieve was determined based on the adsorption isotherm according to the T-plot method, and the pore volume of secondary pores was obtained by subtracting the micropore volume from the total pore volume.

In each of the comparative examples and examples, the surface $SiO_2/Al_2O_3$ molar ratio of the molecular sieve was determined as follows: the percentage by mass of Si and Al atoms on the surface of the molecular sieve was determined by XPS photoelectron spectroscopy, and then the surface $SiO_2/Al_2O_3$ molar ratio of the molecular sieve was calculated. XPS photoelectron spectroscopy was performed on the ESCALab 250 X-ray photoelectron spectrometer of Thermo Scientific Company. The excitation source was monochromated Al Kα X-ray with an energy of 1486.6 eV and a power of 150 W. The penetration energy for narrow scans was 30 eV. The base vacuum at the time of analysis was about 6.5×10$^{-10}$ mbar. The binding energy was calibrated in accordance with the C1s peak (284.8 eV) of alkyl carbon or contaminated carbon.

Unless otherwise stated, the reagents used in each of the comparative examples and examples were chemically pure reagents.

The following Examples 1-6 are directed to the catalytic cracking catalysts containing a rare earth modified Y-type molecular sieve according to the present application.

Example 1

2000 kg (weight on a dry basis) NaY zeolite with a framework $SiO_2/Al_2O_3$ ratio of 4.6 (sodium oxide content 13.5 wt %, Qilu Branch of Sinopec Catalyst Co., Ltd.) was added to a primary exchange tank containing 20 m$^3$ of water and stirred evenly at 25° C. Then, 600 L of $RECl_3$ solution (the rare earth concentration calculated on the basis of $RE_2O_3$ in the $RECl_3$ solution was 319 g/L) was added, and stirring was continued for 60 minutes. The mixture was filtered and washed, and the filter cake was sent to a flash drying oven for drying; a rare earth modified Y-type molecular sieve having a normal lattice constant and a reduced sodium oxide content was obtained, which had a sodium oxide content of 7.0% by weight and a lattice constant of 2.471 nm. Then, the molecular sieve was sent to a roaster and roasted at a temperature of 390° C., in 50% steam atmosphere (an atmosphere containing 50% by volume of steam) for 6 hours, then roasted at a temperature of 500° C., in a dry air atmosphere (containing less than 1% by volume of steam) for 2.5 hours to obtain a Y-type molecular sieve having a reduced lattice constant and a water content of less than 1% by weight, of which the lattice constant was 2.455 nm. Then, the Y-type molecular sieve material having a reduced lattice constant was directly sent to a continuous gas phase ultra-stabilization reactor for gas phase ultra-stabilization reaction. The gas phase ultra-stabilization reaction process of the molecular sieve in the continuous gas phase ultra-stabilization reactor and the subsequent exhaust gas absorption process were carried out in accordance with the method disclosed in Example 1 of the patent application publication No. CN 103787352 A, which is hereby incorporated herein in its entirety, under the following conditions: the weight ratio of $SiCl_4$ to the Y-type molecular sieve was 0.5:1, the feed rate of the molecular sieve was 800 kg/hr, and the reaction temperature was 400° C. The molecular sieve material obtained after the gas phase ultra-stabilization reaction was separated by a gas-solid separator, sent to a secondary exchange tank containing 20 m3 of decationized water added in advance, and stirred evenly. The weight of the molecular sieve material added to the secondary exchange tank was 2000 kg (weight on a dry basis). After that, 0.6 m$^3$ of 10 wt % hydrochloric acid was added slowly, and the reaction mixture was heated to 90° C., and stirred for 60 minutes; then, 140 kg of citric acid was added, and stirring was continued at 90° C. for 60 minutes, followed by filtering, washing, and drying to obtain a modified Y-type molecular sieve product, designated as SZ-1.

Table 1 shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of SZ-1.

After SZ-1 was aged in a bare state at 800° C. in an atmosphere of 100 vol % steam for 17 hours, the relative crystallinity of the molecular sieve SZ-1 before and after aging was analyzed by XRD, and the relative crystallinity retention after aging was calculated. The results are shown in Table 2, in which:

$$\text{Relative crystallinity retention} = \frac{\text{Relative crystallinity of aged sample}}{\text{Relative crystallinity of fresh sample}} \times 100\%$$

1572 g of pseudo-boehmite having an alumina content of 61% by weight was added to 7818 g of deionized water, and 195 ml of chemically pure hydrochloric acid (containing 36% by weight of HCl) was added under stirring, and aged at 70° C. for 1 hour. After that, 165 ml of phosphoric acid (Beijing Chemical Plant, concentration 85%, analytically pure) and 390 g of an aqueous solution of magnesium chloride hexahydrate (Beijing Shuanghuan Reagent Plant, analytically pure) comprising 204 g of magnesium chloride hexahydrate were added and slurried, to obtain a slurry of an additive-containing alumina.

5715 g of an aluminum sol having an alumina content of 21% by weight was added to 15,642 g of decationized water, and then 7302 g of kaolin having a solid content of 76% by weight was added under stirring, and slurried for 60 minutes to obtain a kaolin slurry. 3839 g of pseudo-boehmite having an alumina content of 61% by weight was added to 9381 g of decationized water and slurried; then 231 ml of chemically pure hydrochloric acid (containing 36% by weight of HCl) was added thereto with stirring, and after aging for 60 minutes, the kaolin slurry previously prepared was added, the slurry of the additive-containing alumina previoulsy prepared was further added, and slurried; then 4200 g (dry basis) of SZ-1 molecular sieve and 750 g (dry basis) of REY molecular sieve [Qilu Branch of Sinopec Catalyst Co., Ltd., rare earth content (on the basis of $RE_2O_3$) 18% by weight, silica-alumina ratio (SiO$_2$/Al$_2$O$_3$ molar ratio) 4.6] were added, and slurried. Then, the resultant was spray dried at an inlet temperature of 650° C. and an exhaust gas temperature of 180° C., the resultant was washed with deionized water, and dried to obtain a catalyst, designated as SC-1.

Example 2

2000 kg (weight on a dry basis) NaY zeolite with a framework SiO$_2$/Al$_2$O$_3$ ratio of 4.6 (sodium oxide content 13.5 wt %, Qilu Branch of Sinopec Catalyst Co., Ltd.) was added to a primary exchange tank containing 20 m$^3$ of decationized water, and stirred evenly at 90° C. Then, 800 L of RECl$_3$ solution (the rare earth concentration calculated on the basis of RE$_2$O$_3$ in the RECl$_3$ solution was 319 g/L) was further added, and stirring was continued for 60 minutes. The mixture was filtered and washed, and the filter cake was sent to a flash drying oven for drying to obtain a rare earth modified Y-type molecular sieve having a normal lattice constant and a reduced sodium oxide content, which had a sodium oxide content of 5.5% by weight and a lattice constant of 2.471 nm. Then, the molecular sieve was sent to a roaster and roasted at a temperature (atmosphere temperature) of 450° C. in a 80% steam atmosphere for 5.5 hours; then, the molecular sieve material was passed to a roaster for roasting and drying at a roasting temperature of 500° C. in a dry air atmosphere for a roasting time of 2 hours, where the water content was reduced to less than 1% by weight, to obtain a Y-type molecular sieve having a reduced lattice constant, which had a lattice constant of 2.461 nm. Then, the Y-type molecular sieve material having a reduced lattice constant was directly sent to a continuous gas phase ultra-stabilization reactor for gas phase ultra-stabilization reaction. The gas phase ultra-stabilization reaction process of the molecular sieve in the continuous gas phase ultra-stabilization reactor and the subsequent exhaust gas absorption process were carried out in accordance with the method disclosed in Example 1 of CN103787352A under the following conditions: the weight ratio of SiCl$_4$ to the Y-type molecular sieve was 0.25:1, the feed rate of the molecular sieve was 800 kg/hr and the reaction temperature was 490° C. The molecular sieve material obtained after the gas phase ultra-stabilization reaction was separated by a gas-solid separator, sent to a secondary exchange tank containing 20 m$^3$ of decationized water added in advance, and stirred evenly. The weight of the molecular sieve material added to the secondary exchange tank was 2000 Kg (weight on a dry basis). After that, 0.9 m$^3$ of 7 wt % sulfuric acid solution was added slowly, and the reaction mixture was heated to 93° C., and stirred for 80 minutes; then, 70 kg of citric acid and 50 kg of tartaric acid were added, and stirring was continued at 93° C. for 70 minutes, followed by filtering, washing and drying, to obtain a modified Y-type molecular sieve product, designated as SZ-2.

Table 1 shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of SZ-2.

After SZ-2 was aged in a bare state at 800° C. in an atmosphere of 100 vol % steam for 17 hours, the crystallinity of the molecular sieve SZ-2 before and after aging was analyzed by XRD, and the relative crystallinity retention after aging was calculated. The results are shown in Table 2.

1476 g of pseudo-boehmite having an alumina content of 61% by weight was added to 7344 g of decationized water, and 185 ml of chemically pure hydrochloric acid (containing 36% by weight of HCl) was added under stirring, followed by aging at 70° C. for 1 hour. After that, 1080 g of an aqueous solution of magnesium chloride hexahydrate (Beijing Shuanghuan Reagent Plant, analytically pure) comprising 617 g of magnesium chloride hexahydrate was added, and slurried, to obtain a slurry of an additive-containing alumina.

4284 g of an aluminum sol having an alumina content of 21% by weight was added to 3753 g of decationized water, and 6908 g of kaolin having a solid content of 76% by weight was added thereto with stirring, and slurried for 60 minutes to obtain a kaolin slurry. 4423 g of pseudo-boehmite having an alumina content of 61% by weight was added to 22037 g of decationized water, and 482 ml of hydrochloric acid (chemically pure, concentration: 36% by weight) was added under stirring, and after aging for 60 minutes, the kaolin slurry previously prepared was added, and slurried; the slurry of the additive-containing alumina previously prepared was further added, and slurried; then 4950 g (dry basis) of SZ-2 molecular sieve was added and slurried. Then, spray drying and washing were carried out in the same manner as described in Example 1, followed by drying, to obtain a catalyst SC-2.

Example 3

2000 kg (weight on a dry basis) NaY zeolite with a framework SiO$_2$/Al$_2$O$_3$ ratio of 4.6 (sodium oxide content 13.5 wt %, Qilu Branch of Sinopec Catalyst Co., Ltd.) was added to a primary exchange tank containing 20 m$^3$ of decationized water, and stirred evenly at 95° C. Then, 570 L of RECl$_3$ solution (the rare earth concentration calculated on the basis of RE$_2$O$_3$ in the RECl$_3$ solution was 319 g/L) was further added, and stirring was continued for 60 minutes. Then, the mixture was filtered and washed, and the filter cake was continuously sent to a flash drying oven for drying to obtain a rare earth modified Y-type molecular sieve having a normal lattice constant and a reduced sodium oxide content, which had a sodium oxide content of 7.5% by weight and a lattice constant of 2.471 nm. Then, the molecular sieve was sent to a roaster and roasted at a roasting temperature of 470° C. in an atmosphere containing 70% by volume of steam for 5 hours; then, the molecular sieve material was passed to a roaster for roasting and drying at a roasting temperature of 500° C. in a dry air atmosphere for 1.5 hours, where the water content was reduced to less than 1% by weight, to obtain a Y-type molecular sieve having a reduced lattice constant, which had a lattice constant of 2.458 nm. Then, the Y-type molecular sieve material having a reduced lattice constant was sent to a continuous gas phase ultra-stabilization reactor for gas phase ultra-stabilization reaction. The gas phase ultra-stabilization reaction process of the molecular sieve in the continuous gas phase ultra-stabilization reactor and the subsequent exhaust gas absorption process were carried out in accordance with the method disclosed in Example 1 of CN103787352A under the following conditions: the weight ratio of SiCl$_4$ to the Y-type molecular sieve was 0.45:1, the feed rated of the molecular sieve was 800 kg/hr and the reaction temperature was 400° C. The molecular sieve material obtained after the gas phase ultra-stabilization reaction was separated by a gas-solid separator, sent to a secondary exchange tank containing 20 m$^3$ of decationized water added in advance, and stirred evenly. The weight of the molecular sieve material added to the secondary exchange tank was 2000 Kg (weight on a dry basis). After that, 1.2 m$^3$ of 5 wt % nitric acid was added slowly, the mixture was heated to 95° C., and stirring was continued for 90 minutes; then, 90 kg of citric acid and 40 kg of oxalic acid were added, and stirring was continued at 93° C. for 70 minutes, followed by filtering, washing, and drying, to obtain a modified Y-type molecular sieve product, designated as SZ-3.

Table 1 shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of SZ-3.

After SZ-3 was aged in a bare state at 800° C. in an atmosphere of 100 vol % steam for 17 hours, the crystallinity of the molecular sieve SZ-3 before and after aging was analyzed by XRD, and the relative crystallinity retention after aging was calculated. The results are shown in Table 2.

1968 g of pseudo-boehmite having an alumina content of 61% by weight was added to 9792 g of decationized water, and 246 ml of chemically pure hydrochloric acid (HCl content of 36% by weight) was added under stirring, and aged at 70° C. for 1 hour. After that, 588 ml of phosphoric acid (Beijing Chemical Plant, concentration: 85%, analytically pure) was added, and slurried, to obtain a slurry of an additive-containing alumina.

5712 g of an aluminum sol having an alumina content of 21% by weight was added to 9405 g of decationized water, and 12684 g of kaolin having a solid content of 76% by weight was added thereto with stirring, and slurried for 60 minutes to obtain a kaolin slurry. 7866 g of pseudo-boehmite having an alumina content of 61% by weight was added to 25458 g of decationized water, and 852 ml of chemically pure hydrochloric acid (concentration: 36% by weight) was added under stirring, and after aging for 60 minutes, the kaolin slurry previously prepared was added, and slurried; the slurry of the additive-containing alumina previously prepared was further added, and slurried; then 5,820 g (dry basis) of SZ-3 molecular sieve, 1,863 g (dry basis) of REY molecular sieve [Qilu Branch of Sinopec Catalyst Co., Ltd., rare earth content (on the basis of $RE_2O_3$) 18% by weight, silica-alumina ratio ($SiO_2/Al_2O_3$ molar ratio) 4.6] and 1164 g (dry basis) of ZRP-5 molecular sieve (Qilu Branch of Sinopec Catalyst Co., Ltd., rare earth content 0.5% by weight, silica-alumina ratio 45) were added, and slurried. Then, spray drying and washing were carried out in the same manner as described in Example 1, followed by drying, to obtain a catalyst, designated as SC-3.

Comparative Example 1

2000 g of NaY molecular sieve (dry basis) was added to 20 liters of decationized aqueous solution, stirred evenly, and 1000 g of $(NH_4)_2SO_4$ was added thereto, stirred, and heated to 90-95° C. for 1 hour. Then, the mixture was filtered and washed, and the filter cake was dried at 120° C., and then subjected to hydrothermal modification treatment by roasting at a temperature of 650° C. in a 100% steam atmosphere for 5 hours. Then, the resultant was added to 20 liters of decationized aqueous solution, stirred evenly, and 1000 g of $(NH_4)_2SO_4$ was added thereto, stirred, and heated to 90-95° C. for 1 hour. Then, after filtering and washing, the filter cake was dried at 120° C. and then subjected to a second hydrothermal modification treatment by roasting at a temperature of 650° C. in a 100% steam atmosphere for 5 hours, to obtain a hydrothermally ultra-stabilized Y-type molecular sieve free of rare earth that have undergone two stages of ion-exchange and two stages of hydrothermal stabilization, designated as DZ-1.

Table 1 shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of DZ-1.

After DZ-1 was aged in a bare state at 800° C. in an atmosphere of 100 vol % steam for 17 hours, the crystallinity of the molecular sieve DZ-1 before and after aging was analyzed by XRD, and the relative crystallinity retention after aging was calculated. The results are shown in Table 2.

714.5 g of an aluminum sol having an alumina content of 21% by weight was added to 1565.5 g of decationized water, started stirring, and 2763 g of kaolin having a solid content of 76% by weight was added and dispersed for 60 minutes. 2049 g of pseudo-boehmite having an alumina content of 61% by weight was added to 8146 g of decationized water, and 210 ml of a hydrochloric acid having a concentration of 36% was added under stirring. After 60 minutes of acidification, the dispersed kaolin slurry was added, and then 1500 g (dry basis) of finely ground DZ-1 molecular sieve was added. After stirring evenly, the mixture was spray-dried, washed and dried to obtain a catalyst, designated as DC-1. The DC-1 catalyst obtained comprised, on a dry basis, 30% by weight of DZ-1 molecular sieve, 42% by weight of kaolin, 25% by weight of pseudo-boehmite, and 3% by weight of aluminum sol.

Comparative Example 2

2000 g of NaY molecular sieve (dry basis) was added to 20 liters of decationized aqueous solution, stirred evenly, and 1000 g of $(NH_4)_2SO_4$ was added thereto, stirred, and heated to 90-95° C. for 1 hour. Then, the mixture was filtered and washed, and the filter cake was dried at 120° C., and then subjected to hydrothermal modification treatment by roasting at a temperature of 650° C. in 100% steam atmosphere for 5 hours. Then, the resultant was added to 20 liters of decationized aqueous solution, stirred evenly, 200 ml of $RE(NO_3)_3$ solution (concentration of 319 g/L on the basis of $RE_2O_3$) and 900 g $(NH_4)_2SO_4$ were added thereto, stirred and heated to 90-95° C. for 1 hour. Then, after filtering and washing, the filter cake was dried at 120° C. and then subjected to a second hydrothermal modification treatment by roasting at a temperature of 650° C. in a 100% steam atmosphere for 5 hours, to obtain a hydrothermally ultra-stabilized Y-type molecular sieve containing rare earth that have undergone two stages of ion-exchange and two stages of hydrothermal stabilization, designated as DZ-2.

Table 1 shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pore of DZ-2s.

After DZ-2 was aged in a bare state at 800° C. in an atmosphere of 100 vol % steam for 17 hours, the crystallinity of the molecular sieve DZ-2 before and after aging was analyzed by XRD, and the relative crystallinity retention after aging was calculated. The results are shown in Table 2.

A slurry of the DZ-2 molecular sieve, kaolin, water, pseudo-boehmite binder and aluminum sol was formed in accordance with a conventional method for preparing catalytic cracking catalysts, and spray dried to obtain a microspheroidal catalytic cracking catalyst, designated as DC-2 (in accordance with the method described in Comparative Example 1). The DC-2 catalyst obtained comprised, on a dry basis, 30% by weight of DZ-2 molecular sieve, 42% by weight of kaolin, 25% by weight of pseudo-boehmite, and 3% by weight of aluminum sol.

Comparative Example 3

2000 kg NaY molecular sieve (dry basis) was added to 20 m³ of water, stirred evenly, 650 L of $RE(NO_3)_3$ solution (concentration of 319 g/L on the basis of $RE_2O_3$) was added thereto, stirred, and heated to 90-95° C. for 1 hour. Then, the mixture was filtered and washed, and the filter cake was sent to a flash roaster for roasting and drying, and the roasting was carried out at a temperature of 500° C. in a dry air atmosphere for a roasting time of 2 hours, so that the water content was reduced to less than 1% by weight. Then, the dried molecular sieve material was sent to a continuous gas phase ultra-stabilization reactor for gas phase ultra-stabilization reaction. The gas phase ultra-stabilization reaction process of the molecular sieve in the continuous gas phase ultra-stabilization reactor and the subsequent exhaust gas absorption process were carried out in accordance with the method described in Example 1 of the patent application publication No. CN103787352A under the following conditions: the weight ratio of $SiCl_4$ to the Y-type molecular sieve was 0.4:1, the feed rate of the molecular sieve was 800 kg/hr and the reaction temperature was 580° C. The molecular sieve material obtained after the gas phase ultra-stabilization reaction was separated by a gas-solid separator, sent to a secondary exchange tank containing 20 m³ of water added in advance, and stirred evenly. The weight of the molecular sieve material added to the secondary exchange tank was 2000 kg (weight on a dry basis). After that, 1.2 m³ of 5 wt % nitric acid was added slowly, heated to 95° C., and stirring was continued for 90 minutes; then, 90 kg of citric acid and 40 kg of oxalic acid were added, and stirring was continued at 93° C. for 70 minutes, followed by filtering, washing, and drying, to obtain an ultra-stable rare earth modified Y-type molecular sieve, designated as DZ-3.

Table 1 shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of DZ-3.

After DZ-3 was aged in a bare state at 800° C. in an atmosphere of 100 vol % steam for 17 hours, the crystallinity of the molecular sieve DZ-3 before and after aging was analyzed by XRD, and the relative crystallinity retention after aging was calculated. The results are shown in Table 2.

A slurry of the DZ-3 molecular sieve, kaolin, water, pseudo-boehmite binder and aluminum sol was formed in accordance with a conventional method for preparing catalytic cracking catalysts, and spray dried to obtain a microspheroidal catalytic cracking catalyst, designated as DC-3 (in accordance with the method as described in Comparative Example 1). The DC-3 catalyst obtained comprised, on a dry basis, 30% by weight of the DZ-3 molecular sieve, 42% by weight of kaolin, 25% by weight of pseudo-boehmite, and 3% by weight of aluminum sol.

Comparative Example 4

2000 kg (weight on a dry basis) NaY zeolite having a framework $SiO_2/Al_2O_3$ of 4.6 was added to a primary exchange tank containing 20 m³ of decationized water and stirred evenly at 95° C. Then, 570 L of $RECl_3$ solution (the rare earth concentration calculated on the basis of $RE_2O_3$ in the $RECl_3$ solution was 319 g/L) was added, and stirring was continued for 60 minutes. The mixture was filtered and washed, and the filter cake was continuously sent to a flash drying oven for drying to obtain a rare earth modified Y-type molecular sieve having a normal lattice constant and a reduced sodium oxide content, which had a sodium oxide content of 7.5% by weight and a lattice constant of 2.471 nm. Then, the molecular sieve was sent to a roaster for hydrothermal modification by roasting at a temperature of 650° C. in 100 vol % steam atmosphere for 5 hours; then, the molecular sieve material was passed to a roaster for roasting and drying at a roasting temperature of 500° C. in a dry air atmosphere for a roasting time of 1.5 hours, so that the water content was reduced to less than 1% by weight. Then, the Y-type molecular sieve material having a reduced lattice constant was sent to a continuous gas phase ultra-stabilization reactor for gas phase ultra-stabilization reaction. The gas phase ultra-stabilization reaction process of the molecular sieve in the continuous gas phase ultra-stabilization reactor and the subsequent exhaust gas absorption process were carried out in accordance with the method disclosed in Example 1 of CN103787352A under the following conditions: the weight ratio of $SiCl_4$ to the Y-type molecular sieve was 0.45:1, the feed rate of the molecular sieve was 800 kg/hr and the reaction temperature was 400° C. The molecular sieve material obtained after the gas phase ultra-stabilization reaction was separated by a gas-solid separator, sent to a secondary exchange tank containing 20 m³ of decationized water added in advance, and stirred evenly. The weight of the molecular sieve material added to the secondary exchange tank was 2000 Kg (weight on a dry basis). After that, 1.2 m³ of 5 wt % nitric acid was added slowly, heated to 95° C., and stirring was continued for 90 minutes; then, 90 kg of citric acid and 40 kg of oxalic acid were added, and stirring was continued at 93° C. for 70 minutes, followed by filtering, washing, and drying to obtain an ultra-stable rare earth modified Y-type molecular sieve product, designated as DZ-4.

Table 1 shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of DZ-4.

After DZ-4 was aged in a bare state at 800° C. in an atmosphere of 100 vol % steam for 17 hours, the crystallinity of the molecular sieve DZ-4 before and after aging was analyzed by XRD, and the relative crystallinity retention after aging was calculated. The results are shown in Table 2.

1968 g of pseudo-boehmite having an alumina content of 61% by weight was added to 9792 g of decationized water, and 246 ml of chemically pure hydrochloric acid (HCl content of 36% by weight) was added under stirring, and aged at 70° C. for 1 hour. After that, 588 ml of phosphoric acid (Beijing Chemical Plant, concentration: 85%, analytically pure) was added, and slurried, to obtain a slurry of an additive-containing alumina.

5712 g of an aluminum sol having an alumina content of 21% by weight was added to 9405 g of decationized water, and 12684 g of kaolin having a solid content of 76% by weight was added thereto with stirring, and slurried for 60 minutes to obtain a kaolin slurry. 7866 g of pseudo-boehmite having an alumina content of 61% by weight was added to 25458 g of decationized water, and 852 ml of chemically pure hydrochloric acid (concentration: 36% by weight) was added under stirring. After 60 minutes of aging, the kaolin slurry previously prepared was added and slurried; then the slurry of the additive-containing alumina previously prepared was added and slurried; then, 5,020 g (dry basis) of DZ-4 molecular sieve, 1863 g (dry basis) of REY molecular sieve [Qilu Branch of Sinopec Catalyst Co., Ltd., rare earth content (on the basis of $RE_2O_3$) 18% by weight, silica-alumina ratio ($SiO_2/Al_2O_3$ molar ratio) 4.6] and 1164 g (dry basis) of ZRP-5 molecular sieve (Qilu Branch of Sinopec Catalyst Co., Ltd., rare earth content 0.5% by weight, silica-alumina ratio 45) were added, and slurried. Then, spray drying and washing were carried out in the same manner as described in Example 1, followed by drying, to obtain a catalyst, designated as DC-4.

Comparative Example 5

8000 g of NaY molecular sieve (on a dry basis) was added to 80 liters of decationized aqueous solution, stirred evenly, 2400 ml of $RE(NO_3)_3$ solution (concentration of the rare earth solution was 319 g/L on the basis of RE$_2$O$_3$) was added thereto, stirred, and heated to to 90-95° C. for 1 hour. Then, the mixture was filtered and washed, and the filter cake was dried at 120° C. to obtain a Y-type molecular sieve having a lattice constant of 2.471 nm, a sodium oxide content of 7.0% by weight, and a rare earth content of 8.8% by weight on the basis of RE$_2$O$_3$. Then, the molecular sieve was roasted at a temperature of 390° C. in an atmosphere containing 50% by volume of steam and 50% by volume of air for 6 hours, to obtain a Y-type molecular sieve having a lattice constant of 2.455 nm, followed by drying, to obtain a water content of less than 1% by weight. Then, a gas phase ultra-stabilization reaction process and a subsequent exhaust gas absorption process were carried in accordance with the method disclosed in Example 1 of the patent application publication No. CN103787352A, in which a gaseous SiCl$_4$ vaporied by heat was introduced at a weight ratio of SiCl$_4$ to the Y-type molecular sieve (dry basis) of 0.5:1, and the reaction was conducted for 2 hours at a temperature of 400° C. Then, the resultant was washed with 80 liters of decationized water and then filtered to obtain a modified Y-type molecular sieve, designated as DZ-5, of which the physicochemical properties are shown in Table 1.

After DZ-5 was aged in a bare state at 800° C. in an atmosphere of 100 vol % steam for 17 hours, the relative crystallinity of the molecular sieve DZ-5 before and after aging was analyzed by XRD, and the relative crystallinity retention after aging was calculated. The results are shown in Table 2.

1572 g of pseudo-boehmite having an alumina content of 61% by weight was added to 7818 g of decationized water, and 195 ml of chemically pure hydrochloric acid (containing 36% by weight of HCl) was added under stirring, and aged at 70° C. for 1 hour. After that, 165 ml of phosphoric acid (Beijing Chemical Plant, concentration 85%, analytically pure) and 390 g of an aqueous solution of magnesium chloride hexahydrate (Beijing Shuanghuan Reagent Plant, analytically pure) comprising 204 g of magnesium chloride hexahydrate were added and slurried, to obtain a slurry of an additive-containing alumina.

4998 g of an aluminum sol having an alumina content of 21% by weight was added to 10,950 g of decationized water, and then 5853 g of kaolin having a solid content of 76% by weight was added under stirring, and slurried for 60 minutes to obtain a kaolin slurry. 2631 g of pseudo-boehmite having an alumina content of 61% by weight was added to 9381 g of decationized water, slurried, and then 231 ml of chemically pure hydrochloric acid (containing 36% by weight of HCl) was added thereto with stirring. After 60 minutes of aging, the kaolin slurry previously prepared was added, and then the slurry of the additive-containing alumina previously prepared was added and slurried; then, 2600 g (dry basis) of DZ-5 molecular sieve and 400 g (dry basis) of REY molecular sieve [Qilu Branch of Sinopec Catalyst Co., Ltd., rare earth content (on the basis of RE$_2$O$_3$) 18% by weight, silica-alumina ratio (SiO$_2$/Al$_2$O$_3$ molar ratio) 4.6] were added, and slurried. Then, the resultant was spray dried at a dry gas inlet temperature of 650° C. and an exhaust gas temperature of 180° C., washed with deionized water, and dried to obtain a catalyst, designated as DC-5.

Comparative Example 6

Catalyst DC-6 was prepared in the same manner as described in Example 2, except that molecular sieve DZ-3 obtained in Comparative Example 3 was used in place of molecular sieve SZ-2.

The main properties of the catalytic cracking catalysts obtained in Examples 1-3 and Comparative Examples 1-6 are listed in Table 3. Further, the catalytic cracking catalysts obtained in Examples 1-3 and Comparative Examples 1-6 were evaluated for micro-activity for light oils.

Evaluation of Micro-Activity for Light Oils:

The micro-activity for light oils of each catalyst was evaluated according to the standard method of RIPP 92-90 (see "Petrochemical Analysis Methods (RIPP Test Methods)", edited by Cuiding YANG et al., Science Press, September 1990, First Edition, pp. 263-268), in which the catalyst loading was 5.0 g, the reaction temperature was 460° C., and the feedstock oil was Dagang light diesel oil having a distillation range of 235-337° C. The composition of the product was analyzed by gas chromatography, and the micro-activity for light oils was calculated based on the composition of the product. The results are shown in Table 3.

Micro-activity for light oils (MA)=(production of gasoline below 216° C.+gas production+coke production)/total amount of feed×100%.

Examples 4-6

The catalytic cracking performances of the catalytic cracking catalysts obtained in Examples 1-3 were evaluated, and the results are shown in Table 5.

Evaluation of Cracking Performance for Heavy Oils:

The catalyst was first aged at 800° C. in 100% steam atmosphere for 17 hours, and then evaluated on an ACE (fixed fluidized bed) unit. The feedstock oil was WuHan-mixed-III-2007 (properties shown in Table 4), cracked gas and product oils were collected separately and analyzed by gas chromatography. The catalyst loading was 9 g, the reaction temperature was 500° C., the weight hourly space velocity was 16 h$^{-1}$, and the catalyst-to-oil weight ratio was shown in Table 5.

In the table, conversion=gasoline yield+liquefied gas yield+dry gas yield+coke yield
Light oil yield=gasoline yield+diesel oil yield
Liquid yield=liquefied gas+gasoline+diesel
Coke selectivity=coke yield/conversion.

Comparative Examples 7-12

The catalytic cracking performances of the catalytic cracking catalysts obtained in Comparative Examples 1-6 were evaluated in the same manner as described in the above Examples 4-6, and the results are shown in Table 5.

TABLE 1

Properties of the modified Y-type molecular sieves

| | Example No. | | | | | | | |
|---|---|---|---|---|---|---|---|---|
| | Ex. 1 | Ex. 2 | Ex. 3 | Comp. Ex. 1 | Comp. Ex. 2 | Comp. Ex. 3 | Comp. Ex. 4 | Comp. Ex. 5 |
| Name of molecular sieve | SZ-1 | SZ-2 | SZ-3 | DZ-1 | DZ-2 | DZ-3 | DZ-4 | DZ-5 |
| RE$_2$O$_3$ content/wt % | 5.7 | 8.6 | 6.4 | 0 | 2.7 | 6.2 | 6.0 | 5.7 |
| Na$_2$O content/wt % | 0.26 | 0.29 | 0.22 | 1.3 | 1.5 | 0.79 | 0.18 | 0.51 |

TABLE 1-continued

Properties of the modified Y-type molecular sieves

| | Ex. 1 | Ex. 2 | Ex. 3 | Comp. Ex. 1 | Comp. Ex. 2 | Comp. Ex. 3 | Comp. Ex. 4 | Comp. Ex. 5 |
|---|---|---|---|---|---|---|---|---|
| Total $SiO_2/Al_2O_3$ molar ratio | 10.84 | 8.22 | 9.98 | 4.94 | 4.85 | 10.67 | 11.12 | 9.74 |
| Framework $SiO_2/Al_2O_3$ molar ratio | 11.95 | 8.79 | 10.87 | 10.39 | 7.83 | 11.39 | 12.56 | 11.95 |
| Surface $SiO_2/Al_2O_3$ molar ratio/Framework $SiO_2/Al_2O_3$ molar ratio | <1 | <1 | <1 | <1 | <1 | <1 | <1 | <1 |
| Framework aluminum/Total aluminum × 100 | 90.7 | 93.5 | 91.8 | 47.59 | 61.99 | 93.65 | 88.5 | 81.5 |
| Non-framework aluminum/Total aluminum × 100 | 9.3 | 6.5 | 8.2 | 52.41 | 38.01 | 6.35 | 11.5 | 18.5 |
| Lattice constant/nm | 2.443 | 2.45 | 2.445 | 2.446 | 2.453 | 2.444 | 2.442 | 2.443 |
| crystallinity/% | 71.5 | 72.3 | 75.8 | 60.1 | 59.5 | 58.3 | 56.8 | 63.2 |
| Lattice collapse temperature/° C. | 1081 | 1064 | 1075 | 1038 | 1020 | 1047 | 1051 | 1072 |
| Specific surface area/($m^2$/g) | 648 | 669 | 654 | 615 | 598 | 645 | 625 | 635 |
| Total pore volume/(mL/g) | 0.415 | 0.398 | 0.387 | 0.349 | 0.322 | 0.329 | 0.366 | 0.355 |
| Micropore volume/(mL/g) | 0.259 | 0.280 | 0.275 | 0.255 | 0.249 | 0.309 | 0.247 | 0.281 |
| Pore volume of secondary pores(mL/g) | 0.156 | 0.118 | 0.112 | 0.094 | 0.073 | 0.020 | 0.119 | 0.074 |
| Percentage of pore volume of secondary pores having a pore size of 2.0-100 nm to total pore volume/% | 37.59 | 29.65 | 28.94 | 26.93 | 22.67 | 6.08 | 32.51 | 20.85 |
| Percentage of pore volume of secondary pores of 8.0-100 nm to total pore volume of secondary pores (2.0-100 nm)/% | 75.21 | 68.15 | 59.81 | 18.35 | 16.24 | 1.15 | 65.92 | 15.82 |
| B acid/L acid (total acid conent ratio) | 3.58 | 4.55 | 4.02 | 0.75 | 2.15 | 3.79 | 3.05 | 2.72 |

It can be seen from Table 1 that the highly stable modified Y-type molecular sieve provided in the present application has a low sodium oxide content, a relatively lower non-framework aluminum content at a relatively higher silica-alumina ratio, a relatively higher percentage of the pore volume of secondary pores having a pore size of 2.0-100 nm to the total pore volume, a relatively higher B acid/L acid ratio (the ratio of total B acid content to total L acid content), a relatively higher crystallinity especially when the molecular sieve has a relatively smaller lattice constant and a relatively higher rare earth content, a high lattice collapse temperature, and a high thermal stability.

TABLE 2

Aging test of the modified Y-type molecular sieves

| Example No. | Name of molecular sieve | Relative crystallinity of fresh molecular sieve sample (%) | Relative crystallinity of aged molecular sieve sample (%) (800° C./aged for 17 hours) | Relative crystallinity retention/% |
|---|---|---|---|---|
| Ex. 1 | SZ-1 | 71.5 | 41.84 | 58.52 |
| Ex. 2 | SZ-2 | 72.3 | 38.07 | 52.65 |
| Ex. 3 | SZ-3 | 75.8 | 45.02 | 59.39 |
| Comp. Ex. 1 | DZ-1 | 60.1 | 4.30 | 7.15 |
| Comp. Ex. 2 | DZ-2 | 59.5 | 5.90 | 9.92 |
| Comp. Ex. 3 | DZ-3 | 58.3 | 21.25 | 36.45 |
| Comp. Ex. 4 | DZ-4 | 56.8 | 20.31 | 35.75 |
| Comp. Ex. 5 | DZ-5 | 63.2 | 27.94 | 44.21 |

It can be seen from Table 2 that the modified Y-type molecular sieve provided in the present application shows a relatively higher relative crystallinity retention after being aged in a bare state under severe conditions at 800° C. for 17 hours, indicating that the modified Y-type molecular sieve provided in the present application has a higher hydrothermal stability.

TABLE 3

Properties of the catalytic cracking catalysts

| | Ex. 1 | Ex. 2 | Ex. 3 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|---|
| Name of catalyst | SC-1 | SC-2 | SC-3 | DC-1 | DC-2 | DC-3 | DC-4 | DC-5 | DC-6 |
| Name of molecular sieve | SZ-1 | SZ-2 | SZ-3 | DZ-1 | DZ-2 | DZ-3 | DZ-4 | DZ-5 | DZ-3 |
| $Al_2O_3$ content/wt % | 47.5 | 47.9 | 48.4 | 49.5 | 51.8 | 50.5 | 48.9 | 49.8 | 48.5 |
| $Na_2O$ content/wt % | 0.02 | 0.03 | 0.04 | 0.14 | 0.16 | 0.18 | 0.06 | 0.15 | 0.18 |
| Loss on ignition/wt % | 11.3 | 11.2 | 11.5 | 11.5 | 11.9 | 11.4 | 11.6 | 11.8 | 11.3 |
| Pore volume/(mL·$g^{-1}$) | 0.47 | 0.45 | 0.44 | 0.36 | 0.36 | 0.38 | 0.41 | 0.38 | 0.39 |
| Specific surface area/($m^2$·$g^{-1}$) | 283 | 285 | 291 | 264 | 271 | 287 | 278 | 275 | 286 |
| Abrasion index/(%·$h^{-1}$) | 1.0 | 1.0 | 1.1 | 1.2 | 1.5 | 1.3 | 1.2 | 1.0 | 1.0 |
| Apparent bulk density/(g·$mL^{-1}$) | 0.71 | 0.72 | 0.73 | 0.73 | 0.73 | 0.72 | 0.72 | 0.74 | 0.72 |
| Micro-activity (800° C., 4 h)/% | 86 | 89 | 85 | 41 | 52 | 81 | 82 | 81 | 82 |
| Sieve size distribution/wt % | | | | | | | | | |
| 0-20 μm | 3.5 | 3.2 | 3.4 | 3.3 | 3.3 | 2.9 | 3.1 | 2.8 | 3.0 |
| 0-40 μm | 17.5 | 17.6 | 16.5 | 18.7 | 18.7 | 16.5 | 17.8 | 17.3 | 17.3 |
| 0-149 μm | 91.8 | 92.1 | 91.7 | 92.4 | 92.4 | 91.5 | 91.5 | 92.3 | 91.9 |
| Average pore size (μm) | 71.5 | 72.8 | 70.5 | 69.7 | 69.7 | 72.9 | 70.3 | 71.4 | 72.6 |

TABLE 4

Properties of feedstock oil used in the ACE evaluation

| Name | WuHan-mixed-III-2007 |
|---|---|
| Density (20° C.)/(g·$cm^{-3}$) | 0.9104 |
| Viscosity (80° C.)/($mm^2$/s) | 19.24 |
| Viscosity (100° C.)/($mm^2$/s) | 11.23 |
| Condensation point/° C. | 40 |
| Carbon residue/wt % | 3.11 |
| Saturated hydrocarbons/wt % | 62.3 |
| Aromatics/wt % | 22.7 |
| Colloid/wt % | 14.4 |
| Asphalt/wt % | 0.6 |
| Element mass fraction/% | |
| C | 86.9 |
| H | 12.63 |
| S | 0.61 |
| N | 0.2 |
| Distillation range (D1160)/° C. | |
| Initial boiling point | 267 |
| 5% | 318 |
| 10% | 339 |
| 30% | 407 |
| 50% | 451 |
| 70% | 494 |
| 81.5% | 540 |

TABLE 5

Catalytic cracking performances of the catalytic cracking catalysts

| | Ex. 4 | Ex. 5 | Ex. 6 | Comp. Ex. 7 | Comp. Ex. 8 | Comp. Ex. 9 | Comp. Ex. 10 | Comp. Ex. 11 | Comp. Ex. 12 |
|---|---|---|---|---|---|---|---|---|---|
| Name of catalyst | SC-1 | SC-2 | SC-3 | DC-1 | DC-2 | DC-3 | DC-4 | DC-5 | DC-6 |
| Name of molecular sieve | SZ-1 | SZ-2 | SZ-3 | DZ-1 | DZ-2 | DZ-3 | DZ-4 | DZ-5 | DZ-3 |
| Catalyst-to-oil ratio (weight ratio) | 4 | 4 | 4 | 9 | 8 | 5 | 5 | 4 | 5 |

TABLE 5-continued

Catalytic cracking performances of the catalytic cracking catalysts

| | Ex. 4 | Ex. 5 | Ex. 6 | Comp. Ex. 7 | Comp. Ex. 8 | Comp. Ex. 9 | Comp. Ex. 10 | Comp. Ex. 11 | Comp. Ex. 12 |
|---|---|---|---|---|---|---|---|---|---|
| Product distribution/wt % | | | | | | | | | |
| Dry gas | 1.04 | 0.98 | 1.01 | 1.55 | 1.48 | 1.47 | 1.22 | 1.31 | 1.45 |
| Liquefied gas | 15.41 | 15.81 | 16.09 | 16.86 | 15.33 | 16.31 | 16.75 | 16.67 | 16.32 |
| Coke | 3.51 | 3.65 | 3.7 | 8.33 | 7.61 | 6.19 | 4.45 | 4.51 | 6.01 |
| Gasoline | 56.75 | 56.97 | 57.09 | 38.55 | 43.91 | 51.19 | 53.82 | 53.58 | 51.45 |
| Diesel oil | 16.98 | 16.65 | 16.13 | 20.17 | 19.25 | 16.67 | 16.63 | 16.82 | 16.83 |
| Heavy oils | 6.31 | 5.94 | 5.98 | 14.54 | 12.42 | 8.17 | 7.13 | 7.11 | 7.94 |
| Total | 100 | 100 | 100 | 100 | 100 | 100 | 100 | 100 | 100 |
| Conversion/wt % | 76.71 | 77.41 | 77.89 | 65.29 | 68.33 | 75.16 | 76.24 | 76.07 | 75.23 |
| Coke selectivity/wt % | 4.58 | 4.72 | 4.75 | 12.76 | 11.14 | 8.24 | 5.84 | 5.93 | 7.99 |
| Light oil yield/wt % | 73.73 | 73.62 | 73.22 | 58.72 | 63.16 | 67.86 | 70.45 | 70.4 | 68.28 |
| Total liquid yield/wt % | 89.14 | 89.43 | 89.31 | 75.58 | 78.49 | 84.17 | 87.2 | 87.07 | 84.6 |

It can be seen from Table 5 that the catalytic cracking catalysts prepared according to the present application show a relatively higher conversion, a relatively higher light oil yield and total liquid yield, and excellent coke selectivity. It can be seen that the modified Y-type molecular sieve provided in the present application has a very high hydrothermal stability, a significantly lower coke selectivity, a significantly higher liquid yield, a significantly higher light oil yield, an improved gasoline yield, and a higher conversion activity for heavy oils.

The following Examples 1P-9P are directed to the catalytic cracking catalysts comprising a modified Y-type molecular sieve containing rare earth and phosphorus according to the present application.

Example 1P 2000 kg (weight on a dry basis) NaY zeolite with a framework $SiO_2/Al_2O_3$ ratio of 4.6 (sodium oxide content 13.5 wt %, Qilu Branch of Sinopec Catalyst Co., Ltd.) was added to a primary exchange tank containing 20 m³ of water and stirred evently at 25° C. Then, 600 L of $RECl_3$ solution (the rare earth concentration calculated on the basis of $RE_2O_3$ in the $RECl_3$ solution was 319 g/L) was further added, and stirring was continued for 60 minutes. Then, the mixture was filtered and washed, and the filter cake was continuously sent to a flash drying oven for drying to obtain a rare earth modified Y-type molecular sieve having a normal lattice constant and a reduced sodium oxide content, which had a sodium oxide content of 7.0% by weight and a lattice constant of 2.471 nm. Then, the molecular sieve was sent to a roaster for modification, and the roasting was carried out at an atmosphere temperature controlled at 390° C. in 50% steam atmosphere (an atmosphere containing 50 vol % steam) for 6 hours; then, the molecular sieve material was introduced into a roaster for roasting and drying, and the roasting was carried out at an atmosphere temperature of 500° C. in a dry air atmosphere (steam content of less than 1% by volume) for 2.5 hours, so that the water content was reduced to less than 1% by weight, and a Y-type molecular sieve having a reduced lattice constant was obtained, which had a lattice constant of 2.455 nm. Then, the Y-type molecular sieve material having a reduced lattice constant was directly sent to a continuous gas phase ultra-stabilization reactor for gas phase ultra-stabilization reaction. The gas phase ultra-stabilization reaction process of the molecular sieve in the continuous gas phase ultra-stabilization reactor and the subsequent exhaust gas absorption process were carried out in accordance with the method described in Example 1 of the patent application publication No. CN103787352A under the following conditions: the weight ratio of $SiCl_4$ to the Y-type molecular sieve was 0.5:1, the feed rate of the molecular sieve was 800 kg/hr and the reaction temperature was 400° C. The molecular sieve material obtained after the gas phase ultra-stabilization reaction was separated by a gas-solid separator, sent to a secondary exchange tank containing 20 m³ of decationized water added in advance, and stirred evenly. The weight of the molecular sieve material added to the secondary exchange tank was 2000 kg (weight on a dry basis). After that, 0.6 m³ of 10 wt % hydrochloric acid was added, the mixture was heated to 90° C., and stirring was continued for 60 minutes; then, 140 kg of citric acid was added, and stirring was continued at 90° C. for 60 minutes, followed by filtering and washing. Then, the molecular sieve cake was directly added to an exchange liquid containing ammonium phosphate in such an amount that the weight ratio of phosphorus (calculated on the basis of $P_2O_5$) to the molecular sieve of 0.04, and the weight ratio of water to the molecular sieve was 2.5. The ion-exchange reaction was carried out at 50° C. for 60 minutes, followed by filtering, washing and drying, to obtain a rare earth and phosphorus modified Y-type molecular sieve rich in secondary pores, designated as SZ-1P.

Table 1P shows the composition, lattice constant, relative crystallinity, framework silica-alumina ratio, lattice collapse temperature, specific surface area, percentage of secondary pores having a large pore size (pore size 8-100 nm) to total secondary pores (2-100 nm), and total pore volume of secondary pores of SZ-1P.

After the SZ-1P was aged in a bare state at 800° C. under atmospheric pressure in an atmosphere of 100 vol % steam for 17 hours, the relative crystallinity of the molecular sieve SZ-1P before and after aging was analyzed by XRD, and the relative crystallinity retention after aging was calculated. The results are shown in Table 2P.

1048 g of pseudo-boehmite having an alumina content of 61% by weight was added to 5,212 g of decationized water, and 130 ml of chemically pure hydrochloric acid (containing 36% by weight of HCl) was added under stirring, and aged at 70° C. for 1 hour. After that, 110 ml of phosphoric acid (Beijing Chemical Plant, concentration 85%, analytically pure) and 260 g of aqueous solution of magnesium chloride hexahydrate (Beijing Shuanghuan Reagent Plant, analytically pure) comprising 136 g of magnesium chloride hexahydrate were added, and slurried to obtain a slurry of an additive-containing alumina.

3332 g of an aluminum sol having an alumina content of 21% by weight was added to 7300 g of decationized water, and then 5395 g of kaolin having a solid content of 76% by weight was added under stirring, and slurried for 60 minutes to obtain a kaolin slurry. 1574 g of pseudo-boehmite having an alumina content of 61% by weight was added to 6254 g of decationized water, slurried, and then 154 ml of chemically pure hydrochloric acid (containing 36% by weight of HCl) was added thereto with stirring. After 60 minutes of aging, the kaolin slurry previously prepared was added, and then the slurry of the additive-containing alumina previously prepared was added and slurried; then, 2400 g (dry basis) of SZ-1P molecular sieve and 400 g (dry basis) of REY molecular sieve [Qilu Branch of Sinopec Catalyst Co., Ltd., rare earth content (on the basis of $RE_2O_3$) 18% by weight, silica-alumina ratio ($SiO_2/Al_2O_3$ molar ratio) 4.6] were added, and slurried. Then, the resultant was spray dried at an inlet temperature of 650° C. and an exhaust gas temperature of 180° C., washed with deionized water, and dried to obtain a catalyst, designated as SC-1P.

Example 2P 2000 kg (weight on a dry basis) NaY zeolite with a framework $SiO_2/Al_2O_3$ ratio of 4.6 (sodium oxide content 13.5 wt %, Qilu Branch of Sinopec Catalyst Co., Ltd.) was added to a primary exchange tank containing 20 m³ of decationized water, and stirred evenly at 90° C. Then, 800 L of $RECl_3$ solution (the rare earth concentration calculated on the basis of $RE_2O_3$ in the $RECl_3$ solution was 319 g/L) was further added, and stirring was continued for 60 minutes. The mixture was filtered and washed, and the filter cake was sent to a flash drying oven for drying to obtain a rare earth modified Y-type molecular sieve having a normal lattice constant and a reduced sodium oxide content, which had a sodium oxide content of 5.5% by weight and a lattice constant of 2.471 nm. The molecular sieve was sent to a roaster, and roasted at a temperature (atmosphere temperature) of 450° C. in an 80% steam atmosphere for 5.5 hours; then, the molecular sieve material was passed to a roaster for roasting and drying, and the roasting was carried out at a temperature controlled at 500° C. in a dry air atmosphere for a roasting time of 2 hours, so that the water content of the molecular sieve was reduced to less than 1% by weight and a Y-type molecular sieve having a reduced lattice constant was obtained, which had a lattice constant of 2.461 nm. Then, the Y-type molecular sieve material having a reduced lattice constant was directly sent to a continuous gas phase ultra-stabilization reactor for gas phase ultra-stabilization reaction. The gas phase ultra-stabilization reaction process of the molecular sieve in the continuous gas phase ultra-stabilization reactor and the subsequent exhaust gas absorption process were carried out in accordance with the method disclosed in Example 1 of CN103787352A under the following conditions: the weight ratio of $SiCl_4$ to the Y-type molecular sieve was 0.25:1, the feed rate of the molecular sieve was 800 kg/hr and the reaction temperature was 490° C. The molecular sieve material obtained after the gas phase ultra-stabilization reaction was separated by a gas-solid separator, sent to a secondary exchange tank containing 20 m³ of decationized water added in advance, and stirred evenly. The weight of the molecular sieve material added to the secondary exchange tank was 2000 Kg (weight on a dry basis). After that, 0.9 m³ of 7 wt % sulfuric acid solution was added, the mixture was heated to 93° C., followed by stirring for 80 minutes; then, 70 kg of citric acid and 50 kg of tartaric acid were added, and stirring was continued at 93° C. for 70 minutes, followed by filtering and washing. Then, the molecular sieve cake was directly added to an exchange liquid containing diammonium hydrogen phosphate in such an amount that the weight ratio of phosphorus (calculated on the basis of $P_2O_5$) to the molecular sieve was 0.03, and the weight ratio of water to the molecular sieve was 3.0. The ion-exchange reaction was carried out at 60° C. for 50 minutes, followed by filtering, washing and drying, to obtain an ultra-stable rare earth and phosphorus modified Y-type molecular sieve rich in secondary pores, designated as SZ-2P.

Table 1P shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of SZ-2P.

After SZ-2P was aged in a bare state at 800° C. under atmospheric pressure in an atmosphere of 100 vol % steam for 17 hours, the crystallinity of the molecular sieve SZ-2P before and after aging was analyzed by XRD, and the relative crystallinity retention after aging was calculated. The results are shown in Table 2P.

984 g of pseudo-boehmite having an alumina content of 61% by weight was added to 4896 g of decationized water, and 123 ml of chemically pure hydrochloric acid (containing 36% by weight of HCl) was added under stirring, followed by aging at 70° C. for 1 hour. After that, 720 g of an aqueous solution of magnesium chloride hexahydrate (Beijing Shuanghuan Reagent Plant, analytically pure) comprising 411 g of magnesium chloride hexahydrate was added, and slurried, to obtain a slurry of an additive-containing alumina.

2856 g of an aluminum sol having an alumina content of 21% by weight was added to 2502 g of decationized water, and 5263 g of kaolin having a solid content of 76% by weight was added thereto with stirring, and slurried for 60 minutes to obtain a kaolin slurry. 2949 g of pseudo-boehmite having an alumina content of 61% by weight was added to 14691 g of decationized water, and 321 ml of hydrochloric acid (chemically pure, concentration: 36% by weight) was added under stirring. After 60 minutes of aging, the kaolin slurry previously prepared was added and slurried; then the slurry of the additive-containing alumina previously prepared was added and slurried; then, 3000 g (dry basis) of SZ-2P molecular sieve was added and slurried. Then, spray drying and washing were carried out in the same manner as described in Example 1P, followed by drying, to obtain a catalyst, designated as SC-2P.

Example 3P 2000 kg (weight on a dry basis) NaY zeolite with a framework $SiO_2/Al_2O_3$ ratio of 4.6 (sodium oxide content 13.5 wt %, Qilu Branch of Sinopec Catalyst Co., Ltd.) was added to a primary exchange tank containing 20 m³ of decationized water, and stirred evenly at 95° C., then 570 L of $RECl_3$ solution (the rare earth concentration in $RECl_3$ solution was 319 g/L on the basis of $RE_2O_3$) was further added, and stirring was continued for 60 minutes. Then, the mixture was filtered and washed, and the filter cake was continuously sent to a flash drying oven for drying to obtain a rare earth modified Y-type molecular sieve having a normal lattice constant and a reduced sodium oxide content, which had a sodium oxide content of 7.5% by weight and a lattice constant of 2.471 nm. Then, the molecular sieve was sent to a roaster for hydrothermal modification, in which the roasting was carried out at a roasting temperature of 470° C. in an atmosphere containing 70% by volume of steam for 7 hours; then, the molecular sieve material was passed to a roaster for roasting and drying, and the roasting was carried out at a temperature controlled at 500° C. in a dry air atmosphere for a roasting time of 1.5 hours, so that the water content was reduced to less than 1% by weight, and a Y-type molecular sieve having a reduced lattice constant was obtained, which had a lattice constant of 2.458 nm. Then, the Y-type molecular sieve material having a reduced lattice constant was sent to a continuous gas phase ultra-stabilization reactor for gas phase ultra-stabilization reaction. The gas phase ultra-stabilization reaction process of the molecular sieve in the continuous gas phase ultra-stabilization reactor and the subsequent exhaust gas absorption process were carried out in accordance with the method disclosed in Example 1 of CN103787352A under the following conditions: the weight ratio of $SiCl_4$ to the Y-type molecular sieve was 0.45:1, the feed rated of the molecular sieve was 800 kg/hr and the reaction temperature was 400° C. The molecular sieve material obtained after the gas phase ultra-stabilization reaction was separated by a gas-solid separator, sent to a secondary exchange tank containing 20 m³ of decationized water added in advance, and stirred evenly. The weight of the molecular sieve material added to the secondary exchange tank was 2000 Kg (weight on a dry basis). After that, 1.2 m³ of 5 wt % nitric acid solution was added slowly, the mixture was heated to 95° C., and stirred for 90 minutes; then, 90 kg of citric acid and 40 kg of oxalic acid were added, and the mixture was stirred at 93° C. for 70 minutes, followed by filtering and washing. The molecular sieve cake was directly added to an exchange liquid containing ammonium phosphate in such an amount that the weight ratio of phosphorus (calculated on the basis of $P_2O_5$) to the molecular sieve was 0.015, and the weight ratio of water to the molecular sieve was 2.8. The ion-exchange reaction was carried out at 70° C. for 30 minutes, followed by filtering, washing and drying, to obtain an ultra-stable rare earth and phosphorus modified Y-type molecular sieve rich in secondary pores, designated as SZ-3P.

Table 1P shows the composition, lattice constant, relative crystallinity, framework silica-alumina ratio, lattice collapse temperature, specific surface area, percentage of secondary pores having a large pore size (pore size 80-100 nm) to total secondary pores (pore size 2-100 nm), and total pore volume of secondary pores of SZ-3P.

After SZ-3P was aged in a bare state at 800° C. under atmospheric pressure in an atmosphere of 100 vol % steam for 17 hours, the crystallinity of the molecular sieve SZ-3P before and after aging was analyzed by XRD, and the relative crystallinity retention after aging was calculated. The results are shown in Table 2P.

1312 g of pseudo-boehmite having an alumina content of 61% by weight was added to 6528 g of decationized water, and 164 ml of chemically pure hydrochloric acid (HCl content of 36% by weight) was added under stirring, and aged at 70° C. for 1 hour. After that, 392 ml of phosphoric acid (Beijing Chemical Plant, concentration: 85%, analytically pure) was added, and slurried, to obtain a slurry of an additive-containing alumina.

3808 g of an aluminum sol having an alumina content of 21% by weight was added to 6088 g of decationized water, and 9231 g of kaolin having a solid content of 76% by weight was added thereto with stirring, and slurried for 60 minutes to obtain a kaolin slurry. 5244 g of pseudo-boehmite having an alumina content of 61% by weight was added to 16972 g of decationized water, and 568 ml of chemically pure hydrochloric acid (concentration: 36% by weight) was added under stirring. After 60 minutes of aging, the kaolin slurry previously prepared was added and slurried; then the slurry of the additive-containing alumina previously prepared was added and slurried; then 4000 g (dry basis) of SZ-3P molecular sieve, 539 g (dry basis) of REY molecular sieve (the same as in example 1) and 500 g (dry basis) of ZRP-5 molecular sieve (Qilu Branch of Sinopec Catalyst Co., Ltd., rare earth content 0.5% by weight, silica-alumina ratio 45) were added, and slurried. Then, spray drying and washing were carried out in the same manner as described in Example 1P, followed by drying, to obtain a catalyst, designated as SC-3P.

Comparative Example 1P

A hydrothermally ultra-stabilized Y-type molecular sieve free of rare earth, designated as DZ-1P, and a catalytic cracking catalyst, designated as DC-1P, were prepared in accordance with Comparative Example 1. The DC-1P catalyst obtained comprised 30% by weight of DZ-1P molecular sieve, 42% by weight of kaolin, 25% by weight of pseudo-boehmite, and 3% by weight of aluminum sol.

Table 1P shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of DZ-1P.

After DZ-1P was aged in a bare state at 800° C. under atmospheric pressure in an atmosphere of 100 vol % steam for 17 hours, the crystallinity of the molecular sieve DZ-1P before and after aging was analyzed by XRD, and the relative crystallinity retention after aging was calculated. The results are shown in Table 2P.

Comparative Example 2P

A hydrothermally ultra-stabilized Y-type molecular sieve containing rare earth, designated as DZ-2P, and a catalytic cracking catalyst, designated as DC-2P, were prepared in accordane with Comparative Example 2. The DC-2P catalyst obtained comprised 30% by weight of DZ-2P molecular sieve, 42% by weight of kaolin, 25% by weight of pseudo-boehmite, and 3% by weight of aluminum sol.

Table 1P shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of DZ-2P.

After DZ-2P was aged in a bare state at 800° C. under atmospheric pressure in an atmosphere of 100 vol % steam for 17 hours, the crystallinity of the molecular sieve DZ-2P before and after aging was analyzed by XRD, and the relative crystallinity retention after aging was calculated. The results are shown in Table 2P.

Comparative Example 3P 2000 kg NaY molecular sieve (dry basis) was added to 20 m³ of water, stirred evenly, 650 L of $RE(NO_3)_3$ solution (319 g/L) was added thereto, stirred, and heated to 90-95° C. for 1 hour. Then, the mixture was filtered and washed, and the filter cake was continuously fed to a flash roaster for roasting and drying, and the roasting was carried out at a temperature of 500° C. in a dry air atmosphere for a roasting time of 2 hours, so that the water content was reduced to less than 1% by weight. Then, the dried molecular sieve material was sent to a continuous gas phase ultra-stabilization reactor for gas phase ultra-stabilization reaction. The gas phase ultra-stabilization reaction process of the molecular sieve in the continuous gas phase ultra-stabilization reactor and the subsequent exhaust gas absorption process were carried out in accordance with the method described in Example 1 of the patent application publication No. CN103787352A under the following conditions: the weight ratio of $SiCl_4$ to the Y-type molecular sieve was 0.4:1, the feed rate of the molecular sieve was 800 kg/hr and the reaction temperature was 580° C. The molecular sieve material obtained after the gas phase ultra-stabilization reaction was separated by a gas-solid separator, sent to a secondary exchange tank containing 20 m³ of water added in advance, and stirred evenly. The weight of the molecular sieve material added to the secondary exchange tank was 2000 kg (weight on a dry basis). After that, 1.2 m³ of 5 wt % nitric acid was added slowly, the mixture was heated to 95° C., and stirring was continued for 90 minutes; then, 90 kg of citric acid and 40 kg of oxalic acid were added, and stirring was continued at 93° C. for 70 minutes, followed by filtering and washing. The molecular sieve cake was directly added to an exchange liquid containing ammonium phosphate in such an amount that the weight ratio of phosphorus (calculated on the basis of $P_2O_5$) to the molecular sieve was 0.015, and the weight ratio of water to the molecular sieve was 2.8. The ion-exchange reaction was carried out at 70° C. for 30 minutes, followed by filtering, washing and drying, to obtain an ultra-stable rare earth modified Y-type molecular sieve, designated as DZ-3P.

Table 1P shows the composition, lattice constant, relative crystallinity, framework silica-alumina ratio, lattice collapse temperature, specific surface area, percentage of secondary pores having a large pore size (pore size 8-100 nm) to total secondary pores (pore size 2-100 nm), and total pore volume of secondary pores of DZ-3P.

After DZ-3P was aged in a bare state at 800° C. under atmospheric pressure in an atmosphere of 100 vol % steam for 17 hours, the crystallinity of the molecular sieve DZ-3P before and after aging was analyzed by XRD, and the relative crystallinity retention after aging was calculated. The results are shown in Table 2P.

A slurry of the DZ-3P molecular sieve, kaolin, water, pseudo-boehmite binder and aluminum sol was formed in accordance with a conventional method for preparing catalytic cracking catalysts, and spray dried to obtain a micro-spheroidal catalytic cracking catalyst, designated as DC-3P (in accordance with the method as described in Comparative Example 1). The DC-3P catalyst obtained comprised 30% by weight of DZ-3P molecular sieve, 42% by weight of kaolin, 25% by weight of pseudo-boehmite, and 3% by weight of aluminum sol.

Comparative Example 4P

A catalyst was prepared in accordance with the method as described in Example 2P, except that the molecular sieve DZ-3P obtained in Comparative Example 3P was used in place of the molecular sieve SZ-2P to obtain a catalyst DC-4P.

Examples 4P-6P

The catalysts obtained in Examples 1P-3P were evaluated for micro-activity for light oils. The catalysts SC-1P, SC-2P and SC-3P obtained in Examples 1P-3P were aged at 800° C. in 100% steam atmosphere for 4 hours or 17 hours, respectively, and the micro-activities for light oils of the catalysts were evaluated. The results are shown in Table 3P.

Method for Evaluation of Micro-Activity for Light Oils:

The micro-activity for light oils of each catalyst was evaluated according to the standard method of RIPP 92-90 (see "Petrochemical Analysis Methods (RIPP Test Methods)", edited by Cuiding YANG et al., Science Press, September 1990, First Edition, pp. 263-268), in which the catalyst loading was 5.0 g, the reaction temperature was 460° C., and the feedstock oil was Dagang light diesel oil having a distillation range of 235-337° C. The composition of the product was analyzed by gas chromatography, and the micro-activity for light oils was calculated based on the composition of the product.

Micro-activity for light oils (MA)=(production of gasoline below 216° C.+gas production+coke production)/total amount of feed×100%.

Comparative Example 5P-8P

The catalysts obtained in Comparative Example 1P-4P were evaluated for micro-activity for light oils. The DC-1P, DC-2P, DC-3P and DC-4P catalysts were aged at 800° C. in 100% steam atmosphere for 4 hours or 17 hours, respectively, and their micro-activities for light oils were evaluated. The evaluation method is the same as that described in Examples 4P-6P, and the results are shown in Table 3P.

Examples 7P-9P

Examples 7P-9P illustrate the catalytic cracking performances of the catalytic cracking catalysts according to the present application obtained in Examples 1P-3P.

After aging at 800° C. in a 100% steam atmosphere for 17 hours, the catalytic cracking performances of the SC-1P, SC-2P and SC-3P catalysts were evaluated on a small fixed fluidized bed reactor (ACE), and cracking gas and product oils were collected separately and analyzed by gas chromatography. The catalyst loading was 9 g, the reaction temperature was 500° C., the weight hourly space velocity was 16 h⁻¹, and the catalyst-to-oil weight ratio was shown in Table 5P. The properties of the feedstock used in the ACE test are shown in Table 4P, and the results are shown in Table 5P.

Comparative Examples 9P-12P

Comparative Examples 7P-9P illustrate the catalytic cracking performances of the catalytic cracking catalysts obtained in Comparative Examples 1P-4P.

After aging at 800° C. in a 100% steam atmosphere for 17 hours, the catalytic cracking performances of the DC-1P, DC-2P, DC-3P and DC-4P catalysts were evaluated on a small fixed fluidized bed reactor (ACE). The evaluation method was the same as that described in Examples 7P-9P. The properties of the feedstock used in the ACE test are shown in Table 4P, and the results are shown in Table 5P.

TABLE 1P

Properties of the modified Y-type molecular sieves

| | Example No. | | | | | |
|---|---|---|---|---|---|---|
| | Ex. 1P | Ex. 2P | Ex. 3P | Comp. Ex. 1P | Comp. Ex. 2P | Comp. Ex. 3P |
| Name of molecular sieve | SZ-1P | SZ-2P | SZ-3P | DZ-1P | DZ-2P | DZ-3P |
| $RE_2O_3$ content/wt % | 5.6 | 8.5 | 6.3 | 0 | 2.7 | 6.2 |
| $Na_2O$ content/wt % | 0.09 | 0.14 | 0.12 | 1.3 | 1.5 | 0.79 |
| $P_2O_5$ content/wt % | 3.55 | 2.89 | 1.38 | 0 | 0 | 1.38 |

TABLE 1P-continued

Properties of the modified Y-type molecular sieves

| | Example No. | | | | | |
|---|---|---|---|---|---|---|
| | Ex. 1P | Ex. 2P | Ex. 3P | Comp. Ex. 1P | Comp. Ex. 2P | Comp. Ex. 3P |
| Total $SiO_2/Al_2O_3$ molar ratio | 10.84 | 8.22 | 9.98 | 4.94 | 4.85 | 10.67 |
| Framework $SiO_2/Al_2O_3$ molar ratio | 11.95 | 8.79 | 10.87 | 10.39 | 7.83 | 11.39 |
| Framework aluminum/Total aluminum × 100 | 90.7 | 93.5 | 91.8 | 47.59 | 61.99 | 93.65 |
| Non-framework aluminum/Total aluminum × 100 | 9.3 | 6.5 | 8.2 | 52.41 | 38.01 | 6.35 |
| Lattice constant/nm | 2.443 | 2.45 | 2.445 | 2.446 | 2.453 | 2.444 |
| crystallinity/% | 70.4 | 71.8 | 75.4 | 60.1 | 59.5 | 58.1 |
| Lattice collapse temperature/° C. | 1082 | 1065 | 1077 | 1038 | 1020 | 1047 |
| Specific surface area/($m^2$/g) | 646 | 667 | 654 | 615 | 598 | 645 |
| Total pore volume/(mL/g) | 0.413 | 0.395 | 0.384 | 0.349 | 0.322 | 0.329 |
| Micropore volume/(mL/g) | 0.258 | 0.278 | 0.273 | 0.255 | 0.249 | 0.309 |
| Pore volume of secondary pores having a pore size of 2.0-100 nm/(mL/g) | 0.155 | 0.117 | 0.111 | 0.094 | 0.073 | 0.020 |
| Percentage of pore volume of secondary pores having a pore size of 2.0-100 nm to total pore volume/% | 37.53 | 29.62 | 28.90 | 26.93 | 22.67 | 6.08 |
| Percentage of pore volume of secondary pores of 8.0-100 nm to total pore volume of secondary pores (2.0-100 nm)/% | 75.21 | 68.15 | 59.81 | 18.35 | 16.24 | 1.15 |
| B acid/L acid (total acid conent ratio) | 3.58 | 4.55 | 4.02 | 0.75 | 2.15 | 3.79 |

It can be seen from Table 1P that the highly stable modified Y-type molecular sieve provided in the present application has the following advantages: low sodium oxide content, relatively lower non-framework aluminum content at a relatively higher silica-alumina ratio, higher percentage of pore volume of secondary pores having a pore size of 2.0-100 nm to total pore volume, relatively higher B acid/L acid ratio (the ratio of total B acid content to total L acid content), relatively higher crystallinity when the molecular sieve has a relatively smaller lattice constant and a relatively higher rare earth content, and high thermal stability.

TABLE 2P

Aging test of the modified Y-type molecular sieves

| Example No. | Name of molecular sieve | Relative crystallinity of fresh molecular sieve sample (%) | Relative crystallinity of aged molecular sieve sample (%) (800° C./aged for 17 hours) | Relative crystallinity retention/% |
|---|---|---|---|---|
| Ex. 1P | SZ-1P | 70.4 | 40.37 | 57.34 |
| Ex. 2P | SZ-2P | 71.8 | 37.26 | 51.89 |
| Ex. 3P | SZ-3P | 75.4 | 44.16 | 58.57 |
| Comp. Ex. 1P | DZ-1P | 60.1 | 4.30 | 7.15 |
| Comp. Ex. 2P | DZ-2P | 59.5 | 5.90 | 9.92 |
| Comp. Ex. 3P | DZ-3P | 58.1 | 21.01 | 36.16 |

It can be seen from Table 2P that the modified Y-type molecular sieve provided in the present application shows a relatively higher relative crystallinity retention after being aged in a bare state under severe conditions at 800° C. for 17 hours, indicating that the modified Y-type molecular sieve provided in the present application has a higher hydrothermal stability.

TABLE 3P

Micro-activity of the catalytic cracking catalysts

| Example No. | Name of catalyst | MA (initial) (800° C./ 4 h) | MA (equilibrium) (8000° C./ 17 h) | MA (equilibrium)/ MA (initial) |
|---|---|---|---|---|
| Ex. 4P | SC-1P | 85 | 74 | 87.06 |
| Ex. 5P | SC-2P | 87 | 72 | 82.76 |
| Ex. 6P | SC-3P | 84 | 71 | 84.52 |
| Comp. Ex. 5P | DC-1P | 41 | 18 | 43.90 |
| Comp. Ex. 6P | DC-2P | 52 | 29 | 55.77 |
| Comp. Ex. 7P | DC-3P | 80 | 59 | 73.75 |
| Comp. Ex. 8P | DC-4P | 81 | 60 | 74.07 |

TABLE 4P

Properties of feedstock oil used in the ACE evaluation

| Name | WuHan-mixed-III-2007 |
|---|---|
| Density (20° C.)/(g · cm$^{-3}$) | 0.9104 |
| Viscosity (80° C.)/(mm$^2$/s) | 19.24 |
| Viscosity (100° C.)/(mm$^2$/s) | 11.23 |
| Condensation point/° C. | 40 |
| Carbon residue/wt % | 3.11 |
| Saturated hydrocarbons/wt % | 62.3 |
| Aromatics/wt % | 22.7 |
| Colloid/wt % | 14.4 |
| Asphalt/wt % | 0.6 |
| Element mass fraction/% | |
| C | 86.9 |
| H | 12.63 |
| S | 0.61 |
| N | 0.2 |
| Distillation range (D1160)/° C. | |
| Initial boiling point | 267 |
| 5% | 318 |
| 10% | 339 |
| 30% | 407 |
| 50% | 451 |
| 70% | 494 |
| 81.5% | 540 |

TABLE 5P

Catalytic cracking performances of the catalytic cracking catalysts

| | Example No. | | | | | | |
|---|---|---|---|---|---|---|---|
| | Ex. 7P | Ex. 8P | Ex. 9P | Comp. Ex. 9P | Comp. Ex. 10P | Comp. Ex. 11P | Comp. Ex. 12P |
| Name of catalyst | SC-1P | SC-2P | SC-3P | DC-1P | DC-2P | DC-3P | DC-4P |
| Name of molecular sieve | SZ-1P | SZ-2P | SZ-3P | DZ-1P | DZ-2P | DZ-3P | DZ-3P |
| Catalyst-to-oil ratio (weight ratio) | 4 | 4 | 4 | 9 | 8 | 5 | 5 |
| Product distribution/wt % | | | | | | | |
| Dry gas | 1.29 | 1.31 | 1.25 | 1.55 | 1.48 | 1.41 | 1.39 |
| Liquefied gas | 16.63 | 16.52 | 16.98 | 16.86 | 15.33 | 16.43 | 16.54 |
| Coke | 3.25 | 3.49 | 3.42 | 8.33 | 7.61 | 5.94 | 5.75 |
| Gasoline | 54.97 | 55.91 | 54.16 | 38.55 | 43.91 | 51.81 | 52.05 |
| Diesel oil | 16.77 | 16.46 | 16.94 | 20.17 | 19.25 | 16.46 | 16.43 |
| Heavy oils | 7.09 | 6.31 | 7.25 | 14.54 | 12.42 | 7.95 | 7.84 |
| Total | 100 | 100 | 100 | 100 | 100 | 100 | 100 |
| Conversion/wt % | 76.14 | 77.23 | 75.81 | 65.29 | 68.33 | 75.59 | 75.73 |
| Coke selectivity/wt % | 4.27 | 4.52 | 4.51 | 12.76 | 11.14 | 7.86 | 7.59 |
| Light oil yield/wt % | 71.74 | 72.37 | 71.1 | 58.72 | 63.16 | 68.27 | 68.48 |
| Total liquid yield/wt % | 88.37 | 88.89 | 88.08 | 75.58 | 78.49 | 84.7 | 85.02 |

It can be seen from the results listed in Table 3P and Table 5P that the catalytic cracking catalyst provided in the present application shows a very high hydrothermal stability, a significantly lower coke selectivity, a significantly higher liquid yield, a significantly higher light oil yield, an improved gasoline yield, and a higher heavy oil conversion activity.

In the above description, the concept of the present application has been described with reference to the embodiments. However, it will be understood by those skilled in the art that various modifications and changes can be made without departing from the scope of the present invention defined in the appended claims. Accordingly, the description and drawings should be regarded as illustrative rather than limiting, and all such modifications and changes are covered by the present invention.

It is to be understood that some of the features described separately in a plurality of embodiments for the sake of clarity may also be provided as a combination in a single embodiment. Conversely, a plurality of different features that are described in a single embodiment for the sake of brevity may also be provided separately or in any sub-combination in different embodiments.

The invention claimed is:

1. A catalytic cracking catalyst, comprising from about 10% to about 50% by weight, on a dry basis, of a rare earth modified Y-type molecular sieve, about 2% to about 40% by weight, on a dry basis, of an additive-containing alumina, and about 10% to about 80% by weight, on a dry basis, of clay; wherein the additive-containing alumina comprises, on a dry basis and based on the weight of the additive-containing alumina, about 60% to about 99.5% by weight of alumina and about 0.5% to about 40% by weight of an additive that is one or more selected from the group consisting of compounds containing alkaline earth metal, lanthanide metal, silicon, gallium, boron and/or phosphorus; the rare earth modified Y-type molecular sieve has a rare earth oxide content of about 4% to about 12% by weight, a phosphorus content of about 0% to about 10% by weight on the basis of $P_2O_5$, a sodium oxide content of no more than about 1.0% by weight, a total pore volume of about 0.36 mL/g to about 0.48 mL/g, a percentage of the pore volume of secondary pores having a pore size of 2-100 nm to the total pore volume of the modified Y-type molecular sieve of about 20% to about 40%, a lattice constant of about 2.440-2.455 nm, a percentage of non-framework aluminum content to the total aluminum content of the modified Y-type molecular sieve of no more than about 10%, a lattice collapse temperature of not lower than about 1060° C., and a ratio of B acid to L acid in the total acid content of the modified Y-type molecular sieve of no less than about 3.5, as determined by pyridine adsorption infrared spectroscopy at 200° C.

2. The catalytic cracking catalyst according to claim 1, wherein the rare earth modified Y-type molecular sieve has a percentage of the pore volume of secondary pores having a pore size of 2-100 nm to the total pore volume of about 28% to about 38%.

3. The catalytic cracking catalyst according to claim 1, wherein the rare earth modified Y-type molecular sieve has a percentage of non-framework aluminum content to the total aluminum content of about 5% to about 9.5% by weight, and a framework silica-alumina ratio of about 7 to about 14 calculated on the basis of $SiO_2/Al_2O_3$ molar ratio.

4. The catalytic cracking catalyst according to claim 1, wherein the rare earth modified Y-type molecular sieve has a ratio of B acid to L acid in the total acid content of about 3.5 to about 6, as determined by pyridine adsorption infrared spectroscopy at 200° C.

5. The catalytic cracking catalyst according to claim 1, wherein the rare earth modified Y-type molecular sieve has a relative crystallinity of about 70% to about 80%, and after aging at 800° C. under atmospheric pressure in an atmosphere of 100 vol % steam for 17 hours, the modified Y-type molecular sieve has a relative crystallinity retention of about 38% or more.

6. The catalytic cracking catalyst according to claim 1, wherein the rare earth modified Y-type molecular sieve has a rare earth oxide content of about 4.5% to about 10% by weight, a phosphorus content on the basis of $P_2O_5$ of about 0.1% to about 6% by weight, a sodium oxide content of about 0.05% to about 0.3% by weight, a lattice constant of 2.442-2.451 nm, a framework silica-alumina ratio of about 8.5 to about 12.6 calculated on the basis of $SiO_2/Al_2O_3$ molar ratio.

7. The catalytic cracking catalyst according to claim 1, wherein the modified Y-type molecular sieve has a rare earth oxide content of about 5.5% to about 10% by weight, a sodium oxide content of about 0.15% to about 0.3% by weight, a lattice constant of 2.442-2.453 nm, and a framework silica-alumina ratio of about 7.8 to about 12.6 calculated on the basis of $SiO_2/Al_2O_3$ molar ratio.

8. The catalytic cracking catalyst according to claim 1, wherein the rare earth modified Y-type molecular sieve has a percentage of the total pore volume of secondary pores having a pore size of 8-100 nm to the total pore volume of secondary pores having a pore size of 2-100 nm of about 40% to about 80%.

9. The catalytic cracking catalyst according to claim 1, wherein the catalyst comprises about 25-40% by weight on a dry basis of the rare earth modified Y-type molecular sieve, about 2-20% by weight on a dry basis of the additive-containing alumina, about 5-30% by weight on a dry basis of the alumina binder, and about 30-50% by weight on a dry basis of the clay.

10. A method for the preparation of a catalytic cracking catalyst according to claim 1, comprising the steps of: providing a rare earth modified Y-type molecular sieve, forming a slurry comprising the rare earth modified Y-type molecular sieve, an additive-containing alumina, clay, and water, and spray drying, wherein the additive-containing alumina comprises, based on the weight of the additive-containing alumina, 60% to 99.5% by weight of alumina and 0.5% to 40% by weight of an additive that is one or more selected from the group consisting of compounds containing alkaline earth metal, lanthanide metal, silicon, gallium, boron and/or phosphorus; the rare earth modified Y-type molecular sieve has a rare earth oxide content of about 4% to about 12% by weight, a phosphorus content of about 0% to about 10% by weight on the basis of $P_2O_5$, a sodium oxide content of no more than about 1.0% by weight, a total pore volume of about 0.36 mL/g to about 0.48 mL/g, a percentage of the pore volume of secondary pores having a pore size of 2-100 nm to the total pore volume of the modified Y-type molecular sieve of about 20% to about 40%, a lattice constant of about 2.440 nm to about 2.455 nm, a percentage of non-framework aluminum content to the total aluminum content of the modified Y-type molecular sieve of no more than about 10%, a lattice collapse temperature of not lower than about 1060° C., and a ratio of B acid to L acid in the total acid content of the modified Y-type molecular sieve of no less than about 3.5, as determined by pyridine adsorption infrared spectroscopy at 200° C.

11. The method according to claim 10, wherein the step of providing a rare earth modified Y-type molecular sieve comprises preparing the rare earth modified Y-type molecular sieve by the following steps:
  (1) contacting a NaY molecular sieve with a rare earth salt solution for ion-exchange reaction, to obtain a rare earth modified Y-type molecular sieve having a reduced sodium oxide content;
  (2) subjecting the Y-type molecular sieve obtained in the step (1) to roasting at a temperature of about 350° C. to about 520° C. in an atmosphere containing about 30 vol % to about 90 vol % of steam for about 4.5 hours to about 7 hours, to obtain a Y-type molecular sieve having a reduced lattice constant;

(3) contacting and reacting the Y-type molecular sieve obtained in the step (2) with gaseous silicon tetrachloride at a weight ratio of $SiCl_4$ to the Y-type molecular sieve on a dry basis ranging from about 0.1:1 to about 0.7:1 and a reaction temperature of about 200° C. to 650° C. for a reaction time of about 10 minutes to about 5 hours, to obtain a gas phase ultra-stabilized Y-type molecular sieve;

(4) contacting the modified Y-type molecular sieve obtained in the step (3) with an acid solution; and (5) optionally, subjecting the acid-treated modified Y-type molecular sieve obtained in the step (4) to phosphorus modification by contacting with a phosphorus compound.

12. The method according to claim 11, wherein the rare earth modified Y-type molecular sieve having a reduced sodium oxide content obtained in the step (1) has a lattice constant of about 2.465-2.472 nm, and a sodium oxide content of no more than about 9.0% by weight.

13. The method according to claim 11, wherein the rare earth modified Y-type molecular sieve having a reduced sodium oxide content obtained in the step (1) has a rare earth content of about 4.5% to about 13% by weight on the basis of $RE_2O_3$, a sodium oxide content of about 4.5% to about 9.5% by weight, and a lattice constant of about 2.465-2.472 nm.

14. The method according to claim 11, wherein, in the step (1), the ion-exchange reaction of the NaY molecular sieve with the rare earth solution is carried out under the following conditions: a weight ratio of the NaY molecular sieve:rare earth salt:$H_2O$ of about 1:0.01-0.18:5-20, an ion-exchange temperature of about 15-95° C., and an ion-exchange time of about 30-120 minutes.

15. The method according to claim 11, wherein the rare earth salt is rare earth chloride and/or rare earth nitrate, and the phosphorus compound is one or more selected from the group consisting of phosphoric acid, ammonium phosphate, ammonium dihydrogen phosphate and diammonium hydrogen phosphate.

16. The method according to claim 11, wherein, in the step (2), the roasting temperature is about 380-480° C., the roasting atmosphere is an atmosphere containing about 40-80% steam, and the roasting time is about 5-6 hours.

17. The method according to claim 11, wherein the Y-type molecular sieve having a reduced lattice constant obtained in the step (2) has a lattice constant of about 2.450-2.462 nm, and a water content of no more than about 1% by weight.

18. The method according to claim 11, wherein, in the step (4), the contacting with the acid solution comprises first contacting with an inorganic acid having a medium or higher strength and then contacting with an organic acid, wherein the contacting with the inorganic acid having a medium or higher strength is carried out under the following conditions: a weight ratio of the inorganic acid to the molecular sieve of about 0.01-0.05:1, a weight ratio of water to the molecular sieve of about 5-20:1, a contact time of about 60-120 minutes, and a contact temperature of about 90-98° C.; and the contacting with the organic acid is carried out under the following conditions: a weight ratio of the organic acid to the molecular sieve of about 0.02-0.10:1, a weight ratio of water to the molecular sieve of about 5-20:1, a contact time of about 60-120 minutes and a contact temperature of about 90-98° C.

19. The method according to claim 18, wherein the organic acid is one or more selected from the group consisting of oxalic acid, malonic acid, succinic acid, methyl succinic acid, malic acid, tartaric acid, citric acid, and salicylic acid; the inorganic acid having a medium or higher strength is one or more selected from the group consisting of phosphoric acid, hydrochloric acid, nitric acid and sulfuric acid.

20. The method according to claim 11, wherein the phosphorus modification of the step (5) is carried out by the following: adding the acid-treated modified Y-type molecular sieve obtained in the step (4) to an exchange liquid containing a phosphorus compound to conduct an ion-exchange reaction at about 15-100° C. for about 10-100 minutes; wherein in the mixture formed by the exchange liquid and the molecular sieve, the weight ratio of water to the molecular sieve is about 2-5, and the weight ratio of phosphorus (calculated on the basis of $P_2O_5$) to the molecular sieve is from about 0.0005 to about 0.10.

* * * * *